(12) United States Patent
Awasthi et al.

(10) Patent No.: US 8,827,447 B2
(45) Date of Patent: *Sep. 9, 2014

(54) MONO ETHYLENICALLY UNSATURATED POLYMERIZABLE GROUP CONTAINING POLYCARBOSILOXANE MONOMERS

(71) Applicant: Bausch & Lomb Incorporated, Rochester, NY (US)

(72) Inventors: Alok Kumar Awasthi, Pittsford, NY (US); Jason K. Stanbro, Rochester, NY (US); Jay F. Kunzler, Canandaigua, NY (US); Jeffrey G. Linhardt, Pleasanton, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/781,880

(22) Filed: Mar. 1, 2013

(65) Prior Publication Data

US 2013/0197125 A1 Aug. 1, 2013

Related U.S. Application Data

(63) Continuation-in-part of application No. 12/499,854, filed on Jul. 9, 2009, now Pat. No. 7,994,356, and a continuation of application No. 12/832,174, filed on Jul. 8, 2010, now Pat. No. 8,420,711.

(51) Int. Cl.
*G02C 7/04* (2006.01)
*C08F 236/20* (2006.01)
*C08F 30/08* (2006.01)
*C07F 7/08* (2006.01)
*C08L 83/04* (2006.01)
*C08G 77/50* (2006.01)
*C08G 77/20* (2006.01)

(52) U.S. Cl.
CPC ............... *C08L 83/04* (2013.01); *C07F 7/0852* (2013.01); *C08G 77/20* (2013.01); *C08G 77/50* (2013.01); *C07F 7/0854* (2013.01)
USPC ............ 351/159.24; 351/159.01; 351/159.02; 523/107; 526/306; 526/279

(58) Field of Classification Search
USPC ........... 351/159.01, 159.02, 159.24; 526/306, 526/279; 523/107
See application file for complete search history.

(56) References Cited

U.S. PATENT DOCUMENTS

| | | | |
|---|---|---|---|
| 3,808,179 A | 4/1974 | Gaylord | |
| 4,208,506 A | 6/1980 | Deichert et al. | |
| 4,686,267 A | 8/1987 | Ellis et al. | |
| 4,910,277 A | 3/1990 | Bambury et al. | |
| 5,034,461 A | 7/1991 | Lai et al. | |
| 5,070,215 A | 12/1991 | Bambury et al. | |
| 5,321,108 A | 6/1994 | Kunzler et al. | |
| 5,358,995 A * | 10/1994 | Lai et al. | 524/542 |
| 5,374,662 A | 12/1994 | Lai et al. | |
| 5,387,632 A | 2/1995 | Lai et al. | |
| 5,387,662 A | 2/1995 | Kunzler et al. | |
| 5,420,324 A | 5/1995 | Lai et al. | |
| 5,451,651 A | 9/1995 | Lai | |
| 5,496,871 A | 3/1996 | Lai et al. | |
| 5,539,016 A | 7/1996 | Kunzler et al. | |
| 5,594,085 A | 1/1997 | Lai | |
| 5,610,252 A | 3/1997 | Bambury et al. | |
| 5,639,908 A | 6/1997 | Lai | |
| 5,648,515 A | 7/1997 | Lai | |
| 5,831,110 A | 11/1998 | Isoda et al. | |
| 5,998,498 A | 12/1999 | Vanderlaan et al. | |
| 6,367,929 B1 | 4/2002 | Maiden et al. | |
| 6,384,172 B1 | 5/2002 | Dvornic et al. | |
| 6,921,802 B2 | 7/2005 | Kunzler et al. | |
| 6,943,203 B2 | 9/2005 | Vanderlaan et al. | |
| 7,915,323 B2 | 3/2011 | Awasthi et al. | |
| 8,420,711 B2 * | 4/2013 | Awasthi et al. | 523/107 |
| 2009/0168013 A1 | 7/2009 | Kunzler et al. | |

FOREIGN PATENT DOCUMENTS

| | | |
|---|---|---|
| JP | 2000-131655 A | 5/2000 |
| WO | WO97/20851 | 6/1997 |
| WO | WO2008/092048 | 7/2008 |
| WO | WO2009/009527 | 1/2009 |

OTHER PUBLICATIONS

International Search Report (PCT/ISA/210) and Written Opinion (PCT/ISA/237) mailed on Mar. 30, 2011.
Lai, Yu-Chin. "The Role of Bulky Polysiloxanylalkyl Methacrylates in Oxygen-Permeable Hydrogel Materials" in J. Appl. Poly. Sci., vol. 56, pp. 317-324 (1995).
Lai, Yu-Chin. "The Role of Bulky Polysiloxanylakyl Methacrylates in Polyurethane-Polysiloxane Hydrogels" in J. App. Poly. Sci., vol. 60, pp. 1193-1199 (1996).
Benjamin, William J. et al. "The Oxygen Permeability of Reference Materials" in Optom. Vis. Sci., 74 (12s): 95 (1997).
Lohmeijer, Bas G.G. et al. "Organocatalytic Living Ring-Opening Polymerization of Cyclic Carbosiloxanes" in Organic Letters, vol. 8, No. 21, pp. 4683-4686 (2006).

(Continued)

*Primary Examiner* — Satya Sastri
(74) *Attorney, Agent, or Firm* — Toan P. Vo

(57) ABSTRACT

The present invention relates to polymeric compositions useful in the manufacture of biocompatible medical devices. More particularly, the present invention relates to certain monoethylenically unsaturated polymerizable group containing polycarbosiloxane monomers capable of polymerization to form polymeric compositions having desirable physical characteristics useful in the manufacture of ophthalmic devices.

13 Claims, No Drawings

(56) References Cited

OTHER PUBLICATIONS

Lu, Ping et al. "Reaction of Dimethyldichlorosilane, Phenylmethyldichlorosilane, or Diphenyldichlorosilane with Dimethyl Sulfoxide" in Organometallics, 1996, 15, pp. 4649-4652.
Piccoli, William et al. "Highly Strained Cyclic-Paraffin Siloxanes" in Organic and Biological Chemistry, Apr. 20, 1960, vol. 82, pp. 1883-1885.
Ziatdinov, Vadim et al. Anionic Ring-Opening Polymerization of Trimethylsiloxy-Substituted 1-Oxa-2,5-disilacyclopentanes . . . : in Macromolecules, 2002, vol. 35, pp. 2892-2897.
U.S. Appl. No. 12/499,853, filed Jul. 9, 2009, Awasthi et al.
U.S. Appl. No. 12/499,854, filed Jul. 9, 2009, Awasthi et al.
Office Action received in corresponding Japanese Application No. 2012-519720 dated Mar. 31, 2014 English translation was provided by Sewa Patent & Law (14 pages).

* cited by examiner

MONO ETHYLENICALLY UNSATURATED POLYMERIZABLE GROUP CONTAINING POLYCARBOSILOXANE MONOMERS

PRIORITY CLAIMS TO PRIOR APPLICATIONS

This patent application is a continuation in part of U.S. patent application Ser. No. 12/499,854 filed on Jul. 9, 2009 and a continuation of U.S. patent application Ser. No. 12/832,174 filed on Jul. 8, 2010; the contents of each of which are incorporated by reference herein.

FIELD

The present invention relates to novel monomers useful in the manufacture of biocompatible medical devices. More particularly, the present invention relates to certain monomers based on mono ethylenically unsaturated polymerizable group containing polycarbosiloxane monomers capable of polymerization to form polymeric compositions having desirable physical characteristics useful in the manufacture of ophthalmic devices. Such characteristics include low modulus of elasticity, improved lubricity and improved hydrolytic stability.

BACKGROUND AND SUMMARY

Various articles, including biomedical devices, are formed of organosilicon-containing materials. One class of organosilicon-containing materials useful for biomedical devices, such as soft contact lenses, is silicone-containing hydrogel materials. A hydrogel is a hydrated, crosslinked polymeric system that contains water in an equilibrium state. Hydrogel contact lenses offer relatively high oxygen permeability as well as desirable biocompatibility and comfort. The inclusion of a silicone-containing material in the hydrogel formulation generally provides higher oxygen permeability since silicone based materials have higher oxygen permeability than water.

Organosilicon-containing materials useful for biomedical devices, including contact lenses, are disclosed in the following U.S. patents: U.S. Pat. No. 4,208,506 (Deichert et al.); U.S. Pat. No. 4,686,267 (Ellis et al.); U.S. Pat. No. 5,034,461 (Lai et al.); and U.S. Pat. No. 5,070,215 (Bambury et al.).

U.S. Pat. Nos. 5,358,995 and 5,387,632 describe hydrogels made from various combinations of silicone macromers, TRIS, n-vinyl pyrrolidone (NVP) and DMA. Replacing a substantial portion of the silicone macromer with TRIS reduced the modulus of the resulting hydrogels. Two publications from the same author, "The Role of Bulky Polysiloxanylalkyl Methacrylates in Polyurethane-Polysiloxane Hydrogels", *J. Appl. Poly. Sci.*, Vol. 60, 1193-1199 (1996), and "The Role of Bulky Polysiloxanylalkyl Methacrylates in Oxygen-Permeable Hydrogel Materials", *J. Appl. Poly. Sci.*, Vol. 56, 317-324 (1995) also describe experimental results indicating that the modulus of hydrogels made from reaction mixtures of silicone-macromers and hydrophilic monomers such as DMA decreases with added TRIS. The addition of methacryloxypropyltris(trimethylsiloxy)silane (TRIS) reduced the modulus of such hydrogels, but in many examples the modulus was still higher than may be desired.

U.S. Pat. No. 4,208,506 describes monomeric polyparaffinsiloxanes capped with activated unsaturated groups and polymers and copolymers thereof. The monomers of U.S. Pat. No. 4,208,506 are cross-linkers. However, there still remains a need in the art for new monomers to provide silicone hydrogels which are soft enough to make soft contact lenses, which possess high oxygen permeability, suitable water content, and sufficient elasticity, and are comfortable to the contact lens wearer.

BRIEF DESCRIPTION OF THE DRAWINGS

None.

DETAILED DESCRIPTION

Unless clearly stated otherwise all materials used in forming a monomer mix are listed as weight percent. Also, unless clearly stated otherwise it will be understood that all amounts of materials used to make the monomers and monomer mixes disclosed herein represent the statistical mean of a normal distribution of weight values such as are ordinarily encountered in the laboratory or commercial manufacture of the monomers and monomer mixes disclosed herein. Therefore, unless clearly stated otherwise, all numerical values shall be understood as being modified by the term "about".

As used herein the expressions "polycarbosiloxane monomer" or "EDS" refer to monomers having at least one -[silyl-alkyl-siloxanyl]- group. The -[silyl-alkyl-siloxanyl]- group may be substituted at any atom capable of having a substituent group and the -[silyl-alkyl siloxanyl]- group may be a repeating group. The alkyl portion of the -[silyl-alkyl-siloxanyl]- group is a linking group between the silyl and siloxanyl group and is preferably 2-7 carbon atoms in length.

The term "monomer" used herein refers to varying molecular weight compounds (i.e. typically having number average molecular weights from about 300 to about 100,000) that can be polymerized, and to medium to high molecular weight compounds or polymers, sometimes referred to as macromonomers, (i.e., typically having number average molecular weights greater than 600) containing functional groups capable of further polymerization. Thus, it is understood that the terms "organosilicon-containing monomers", "silicone-containing monomers" and "hydrophilic monomers" include monomers, macromonomers and prepolymers. Prepolymers are partially polymerized monomers or monomers which are capable of further polymerization.

An "organosilicon-containing monomer" contains at least one [siloxanyl] or at least one [silyl-alkyl-siloxanyl] repeating units, in a monomer, macromer or prepolymer. Preferably, the total Si and attached O are present in the organosilicon-containing monomer in an amount greater than 5 weight percent, and more preferably greater than 30 weight percent of the total molecular weight of the organosilicon-containing monomer. A "silicone-containing monomer" is one that contains at least one [siloxanyl] repeating units, in a monomer, macromer or prepolymer.

In a first aspect, the invention relates to monomers of formula (I):

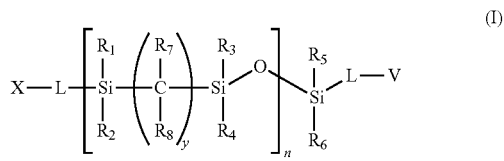

wherein X is the residue of a ring opening agent or a capping agent; L is the same or different and is a linker group or a bond; V is an ethylenically unsaturated polymerizable group; $R_1$, $R_2$, $R_3$, $R_4$, $R_5$, $R_6$ are independently H, alkyl, halo alkyl, heteroalkyl, cyclo alkyl, heterocyclo alkyl, alkenyl, halo alkenyl, or aromatic; $R_7$ and $R_8$ when present are independently H or alkyl wherein at least one of $R_7$ or $R_8$ is hydrogen; y is 2-7 and n is 1-100.

Ring opening agents are well known in the literature. Non-limiting examples of anionic ring opening agents include alkyl lithiums, alkoxides, trialkylsiloxylithium wherein the alkyl group may or may not contain halo atoms.

Capping agents are well known in the literature. Non-limiting examples of capping agents include 3-methacryloxypropyldimethylchlorosilane, 3-acryloxypropyl dimethylchlorosilane, chlorodimethylsilane and bromodimethylsilane.

Linker groups can be any divalent radical or moiety and include substituted or unsubstituted alkyl, alkyl ether, alkenyls, alkenyl ethers, halo alkyls, substituted or unsubstituted siloxanes, and monomers capable of propagating ring opening.

Ethylenically unsaturated polymerizable groups are well known to those skilled in the art. Non-limiting examples of ethylenically unsaturated polymerizable groups would include acrylates, methacrylates, vinyl carbonates, O-vinyl carbamates, N-vinyl carbamates, acrylamides and methacrylamides.

Additional preferred embodiments of the monomers of the invention herein would include monomers of formula (II):

(II)

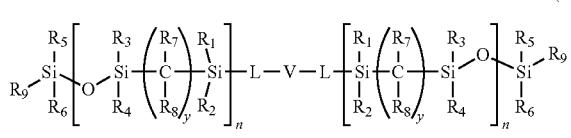

wherein L is the same or different and is a linker group or a bond; V is an ethylenically unsaturated polymerizable group; $R_1$, $R_2$, $R_3$, $R_4$, $R_5$, $R_6$ and $R_9$ are independently H, alkyl, halo alkyl, cyclo alkyl, heterocyclo alkyl, alkenyl, halo alkenyl, or aromatic; $R_7$ and $R_8$ when present are independently H or alkyl wherein at least one of $R_7$ or $R_8$ is hydrogen; y is 2-7 and n is 1-100.

Additional preferred embodiments of the monomers of the invention herein would include monomers of the following formulas III and IV:

(III)

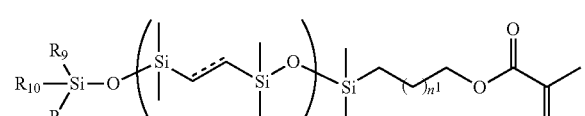

wherein $R_9$, $R_{10}$ and $R_{11}$ are independently H, alkyl, haloalkyl or other substituted alkyl groups; n is as defined above and $n^1$ is 0-10; and, (IV)

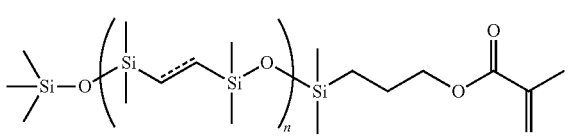

wherein n is 1-100, preferably n is 2-80, more preferably n is 3-20, most preferably n is 5-15.

Additional preferred embodiments of the monomers of the invention herein would include monomers of the following formulas V-IX:

(M1-EDS6-TMS)

(V)

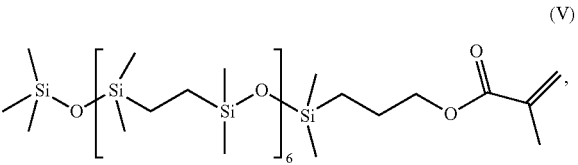

(M1-EDS7-TMS)

(VI)

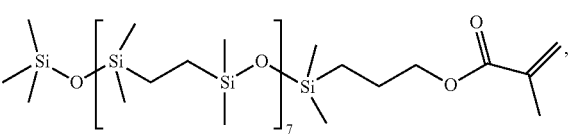

(M1-EDS9-TMS)

(VII)

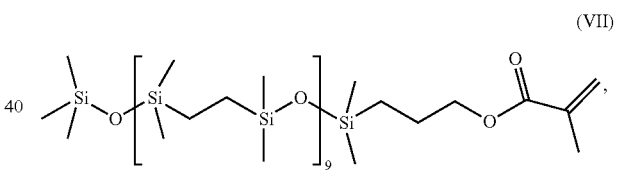

(M1-EDS12-TMS)

(VIII)

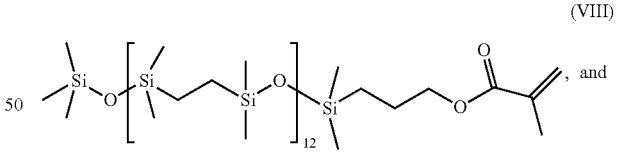

(M1-EDS15-TMS)

(IX)

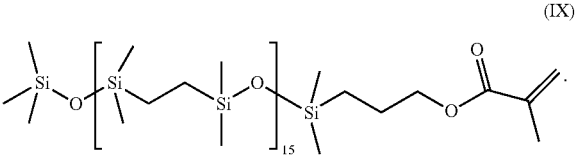

Additional preferred embodiments of the monomers of the invention herein would include monomers of the following formulas X-XII:

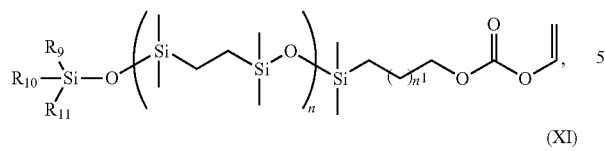

(X)

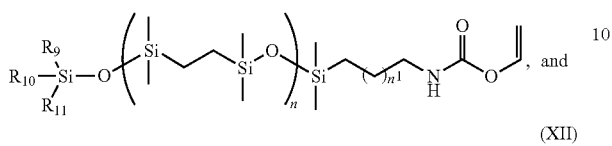

(XI)

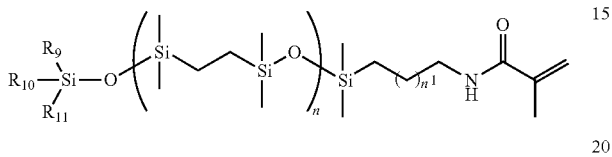

(XII)

wherein $R_9$, $R_{10}$ and $R_{11}$ are independently H, alkyl, haloalkyl or other substituted alkyl groups and n and $n^1$ are as defined above.

Additional preferred embodiments of the monomers of the invention herein would include monomers of the following formulas XIII-XV:

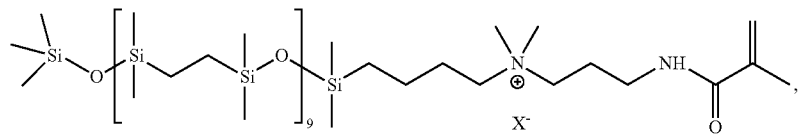

(XIII)

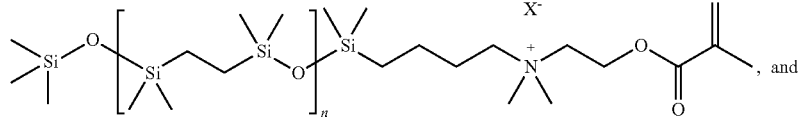

(XIV)

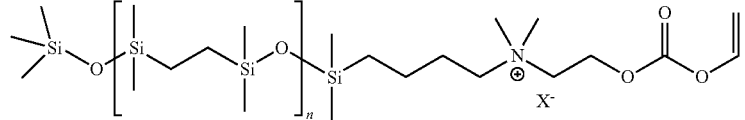

(XV)

wherein n is as defined above and X is a counterion to provide an overall neutral charge.

Counterions capable of providing an overall neutral charge are well known to those of ordinary skill in the art and would include, for example, halide and borate ions.

An additional preferred embodiment of the monomers of the invention herein would include the monomer of the following formula XVI:

(M1-EDS7-D37-TMS)

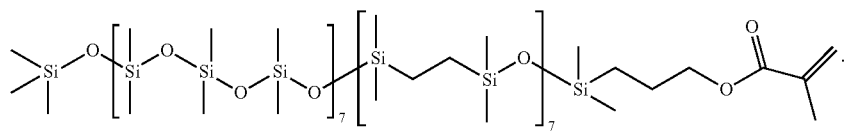

(XVI)

Monomers of formula I can be prepared by various synthetic methods, for example:
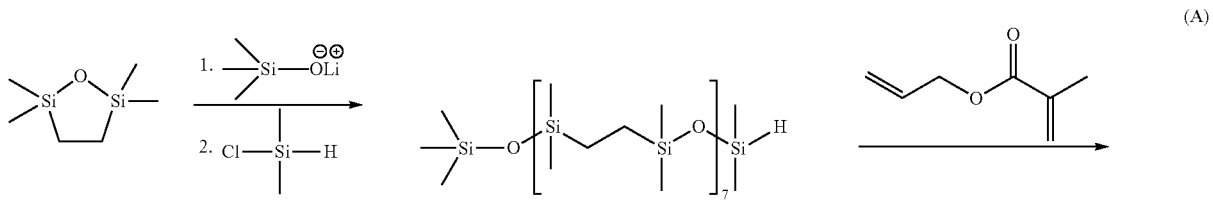
(A)
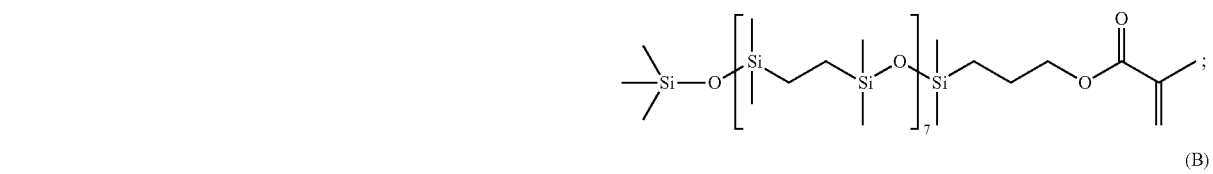
(B)
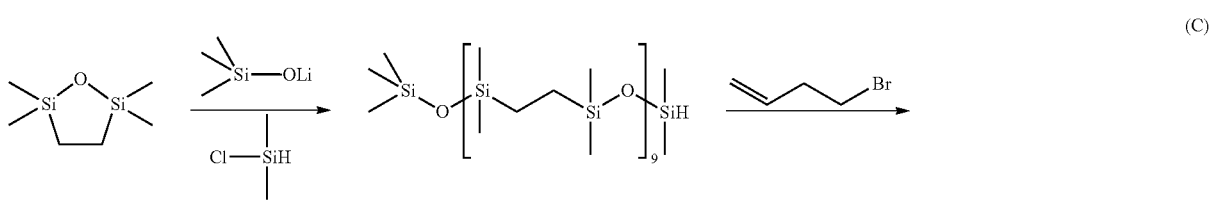
(C)
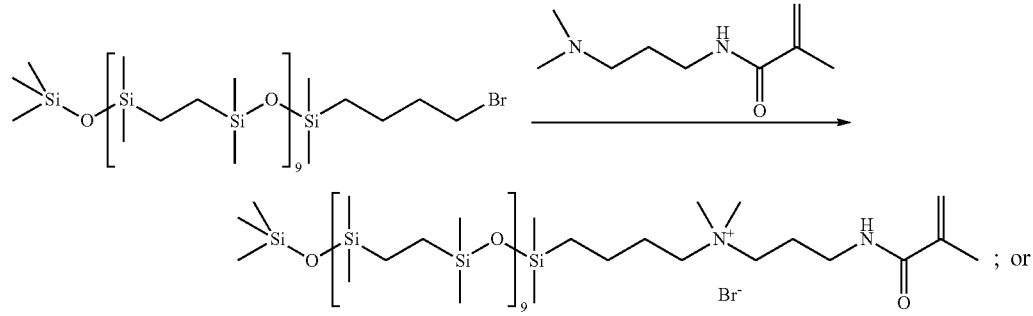
; or
(D)
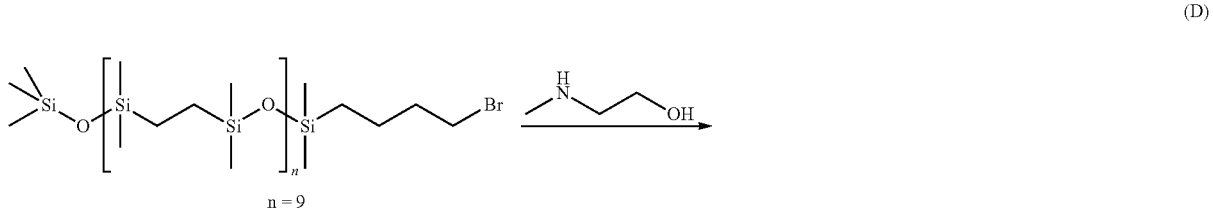
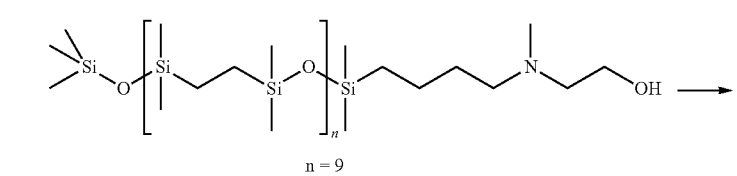
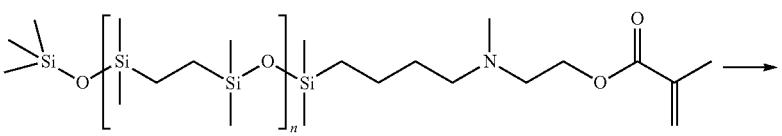

-continued

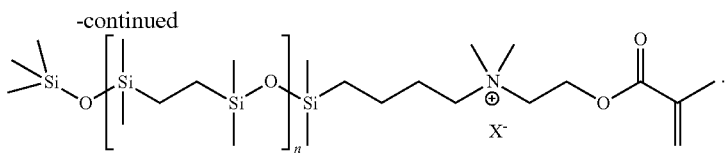

Monomers of formula II can be prepared by various synthetic methods, for example as shown in Example 6.

In yet another aspect, the invention includes articles formed of device forming monomer mixes comprising, alone or in combination, any of the monomers of formulas I-XVI. According to preferred embodiments, the article is the polymerization product of a mixture comprising at least one of the aforementioned monomers of formulas I-XVI and at least a second copolymerizable monomer. The invention is applicable to a wide variety of polymeric materials, either rigid or soft ophthalmic materials for implantation on or in an eye. Especially preferred polymeric materials are ophthalmic lenses including contact lenses, phakic and aphakic intraocular lenses and corneal implants although all polymeric materials including biomaterials are contemplated as being within the scope of this invention. Preferred articles are optically clear and useful as a contact lens.

The monomer mix of the present invention also provides medical devices such as artificial heart valves, buttons for lathing lenses, films, surgical devices, vessel substitutes, intrauterine devices, membranes, diaphragms, surgical implants, artificial blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially hydrogel contact lenses.

As set forth above, unless clearly stated otherwise it will be understood that all amounts of materials used to make the monomers and monomer mixes disclosed herein represent the statistical mean of a normal distribution of weight values such as are ordinarily encountered in the laboratory or commercial manufacture of the monomers and monomer mixes disclosed herein. Therefore, unless clearly stated otherwise, all numerical values shall be understood as being modified by the term "about".

Useful concentration of the mono ethylenically unsaturated polymerizable group containing polycarbosiloxane monomers of the invention herein would be 0.1 to percent by weight of the monomer mix. More preferred concentrations are 0.1 to 20 percent by weight. Even more preferred concentrations would be 5 to 15 percent by weight.

Preferred compositions of the monomer mix have both hydrophilic and hydrophobic monomers. Depending upon the specific application, useful articles made with these materials may require additional (other than the subject mono ethylenically unsaturated polymerizable group containing polycarbosiloxane monomers) hydrophobic, possibly silicone containing monomers. These additional silicone containing hydrophobic monomers will be present at between 0.1 to 75.8 percent by weight, more preferably between 2 to 20 percent by weight, even more preferably between 5 to 13 percent by weight. Amounts of non-silicone containing hydrophobic monomers will be 0 to 60 percent by weight. Examples of non-silicone hydrophobic materials include alkyl acrylates and methacrylates. Especially preferred is silicone-containing hydrogel forming materials.

Depending upon the application, useful articles may also require bulky monomers such as those disclosed in U.S. Pat. No. 6,921,802 which include methacryloxypropyl tris(trimethylsiloxy)silane ("TRIS"), pentamethyldisiloxanyl methylmethacrylate, tris(trimethylsiloxy)methacryloxy propylsilane, phenyltretramethyl-disloxanylethyl acrylate, methyldi (trimethylsiloxy)methacryloxymethyl silane, 3-[tris (trimethylsiloxy)silyl]propyl vinyl carbamate, 3-[tris (trimethylsiloxy)silyl]propyol allyl carbamate, and 3-[tris (trimethylsiloxy)silyl]propyl vinyl carbonate. These bulky monomers, when present, may be present at 0 to 41.2 percent by weight, 34 to 41 percent by weight or even 25 to 41 percent by weight.

Organosilicon-containing hydrogels are prepared by polymerizing a mixture containing at least one organosilicon-containing monomer and at least one hydrophilic monomer. Additionally, a silicone-containing monomer which functions as a crosslinking agent (a crosslinker being defined as a monomer having multiple polymerizable functionalities) or a separate crosslinker may be employed. Hydrophobic crosslinkers would include methacrylates such as ethylene glycol dimethacrylate (EGDMA) and allyl methacrylate (AMA). Methacrylamide crosslinkers such as Ma2D37 allow the incorporation of greater amounts hydrophilic comonomers into the monomer mix than its methacrylate counterparts. This greater amount of hydrophilic comonomers provides a finished lens with higher water content and improved wetability. Amounts of cross-linker would be between 0 to 76 percent by weight, 2 to 20 percent by weight or 5 to 13 percent by weight.

The mono ethylenically unsaturated polymerizable group containing polycarbosiloxane monomers of the invention herein may be copolymerized with a wide variety of hydrophilic monomers to produce silicone hydrogel lenses. Suitable hydrophilic monomers include: unsaturated carboxylic acids, such as methacrylic and acrylic acids; acrylic substituted alcohols, such as 2-hydroxyethyl methacrylate and 2-hydroxyethyl acrylate; vinyl lactams, such as N-vinylpyrrolidone (NVP) and 1-vinylazonan-2-one; and acrylamides, such as methacrylamide and N,N-dimethylacrylamide (DMA). These hydrophilic monomers will be present, separately or by combined weight in amounts of between 0 to 60 percent by weight, between 20 to 45 percent by weight, between 0 to 48.6 percent by weight, between 0 to 30 percent by weight, between 0 to 25 percent by weight, between 0 to 9.5 percent by weight or between 2 to 7 percent by weight.

Other examples of silicone-containing monomer mixtures which may be used with this invention include the following: vinyl carbonate and vinyl carbamate monomer mixtures as disclosed in U.S. Pat. Nos. 5,070,215 and 5,610,252 (Bambury et al); fluorosilicon monomer mixtures as disclosed in U.S. Pat. Nos. 5,321,108; 5,387,662 and 5,539,016 (Kunzler et al.); fumarate monomer mixtures as disclosed in U.S. Pat. Nos. 5,374,662; 5,420,324 and 5,496,871 (Lai et al.) and urethane monomer mixtures as disclosed in U.S. Pat. Nos. 5,451,651; 5,648,515; 5,639,908 and 5,594,085 (Lai et al.), all of which are commonly assigned to assignee herein Bausch & Lomb Incorporated, and the entire disclosures of which are incorporated herein by reference. Other suitable hydrophilic monomers will be apparent to one skilled in the art.

An organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include alcohols such as tert-butanol (TBA), tert-amyl alcohol, hexanol and nonanol; diols, such as ethylene glycol; and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect (for example, minimal phase separation of polymerized products). Generally, the diluent is included at 0 to 60% by weight of the monomeric mixture, with 1 to 40% by weight being more preferred, 2 to 30% by weight being even more preferred and 3 to 25% by weight being especially preferred.

According to the present process, the monomeric mixture, comprising at least one hydrophilic monomer, at least one mono ethylenically unsaturated polymerizable group containing polycarbosiloxane monomer and optionally the organic diluent, is shaped and cured by conventional methods such as static casting or spincasting.

Lens formation can be by free radical polymerization using initiators such as azobisisobutyronitrile (AIBN) and peroxide catalysts under conditions such as those set forth in U.S. Pat. No. 3,808,179, incorporated herein by reference. Photoinitiation of polymerization of the monomer mixture using initiators such as IRGACURE 819 (Bis(2,4,6-trimethylbenzoyl)-phenylphosphineoxide) and DAROCURE 1173 (2-Hydroxy-2-methyl-1-phenyl-propan-1-one) are also well known in the art and may be used in the process of forming an article as disclosed herein. By careful selection of the appropriate wavelength of light to conduct photo polymerization of the monomer mix a finished product having desirable properties such as surface hydrophilicity and surface lubricity can result. Other reaction conditions important to photo polymerization would include incident light intensity, light exposure time and controlled atmosphere can also be critical to providing a successful commercial product. Suitable light intensity will depend upon polymerization conditions such as the mold material, monomer mix and initiator concentration ratio. For example, suitable intensities would range from 1.0 mW/cm2 to 25.0 mW/cm2. Similarly, light exposure time can vary, depending upon polymerization conditions. Therefore, light exposure time may range from one minute to 60 minutes. Control of atmospheric conditions for polymerizing contact lenses is well known in the art. Colorants and the like may be added prior to monomer polymerization.

Subsequently, a sufficient amount of unreacted monomer and, when present, organic diluent is removed from the cured article to improve the biocompatibility of the article. Release of non-polymerized monomers into the eye upon installation of a lens can cause irritation and other problems. Therefore, once the biomaterials formed from the polymerized monomer mix containing the monomers disclosed herein are formed they are then extracted to prepare them for packaging and eventual use. Extraction is accomplished by exposing the polymerized materials to various solvents such as water, 2-propanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water, buffer solution or other packaging solution.

Surface structure and composition determine many of the physical properties and ultimate uses of solid materials. Characteristics such as wetting, friction, and adhesion or lubricity are largely influenced by surface characteristics. The alteration of surface characteristics is of special significance in biotechnical applications where biocompatibility is of particular concern. It should be remembered that in coating medical devices the term "surface" is not to be limited to meaning "at least one complete surface". Surface coverage does not have to be even or complete to be effective for surface functionality or surface treatment. Thus, it is desired to provide an organosilicon containing hydrogel contact lens with an optically clear, hydrophilic surface film that will not only exhibit improved wetability, but which will generally allow the use of an organosilicon containing hydrogel contact lens in the human eye for extended period of time. In the case of a organosilicon containing hydrogel lens for extended wear, it may be further desirable to provide an improved organosilicon-containing hydrogel contact lens with an optically clear surface film that will not only exhibit improved lipid and microbial behavior, but which will generally allow the use of a organosilicon-containing hydrogel contact lens in the human eye for an extended period of time. Such a surface treated lens would be comfortable to wear in actual use and allow for the extended wear of the lens without irritation or other adverse effects to the cornea.

It may also be desirable to apply these surface enhancing coatings to implantable medical devices such as intraocular lens materials to reduce the attachment of lens epithelial cells to the implanted device and to reduce friction as the intraocular lens passes through an inserter into the eye. Therefore, if needed to produce a successful commercial product the polymerized materials may optionally be coated.

Methods of coating contact lenses and various types of coatings for contact lenses are well known to those of ordinary skill in the art. Methods of coating the substrate include dip coating of the substrate into a solution containing the surface coating material. The solution containing the surface coating material may contain substantially the surface coating material in solvent or may contain other materials such as cleaning and extracting materials. Other methods could include spray coating the device with the surface coating material. In certain embodiments, it may be necessary to use suitable catalysts, for example, a condensation catalyst. Alternatively, the substrate and the other surface coating material may be subjected to autoclave conditions. In certain embodiments, the substrate and the surface coating material may be autoclaved in the packaging material that will contain the coated substrate. Once the interaction between the substrate and the surface coating material has occurred, the remaining surface modifying agent could be substantially removed and packaging solution added to the substrate packaging material. Sealing and other processing steps then proceed as they usually do. Alternatively, the surface modifying agent could be retained in the substrate packaging material during storage and shipping of the substrate device to the end user.

Coatings for medical devices are typically oligomeric or polymeric and sized to provide suitable properties to the surface of the medical device to be coated. Coatings according to certain embodiments of the invention herein will typically contain hydrophilic domain(s) showing good surface properties when the coating is associated with the substrate (i.e., the uncoated medical device). The hydrophilic domain(s) will comprise at least one hydrophilic monomer, such as, HEMA, glyceryl methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), or derivatives thereof. Still further examples are the hydrophilic vinyl carbonate or vinyl carbamate monomers. Hydrophilic monomers can be nonionic monomers, such as 2-hydroxyethyl methacrylate ("HEMA"), 2-hydroxyethyl acrylate ("HEA"), 2-(2-ethoxyethoxy)ethyl(meth)acrylate, glyceryl(meth)acrylate, poly(ethylene glycol(meth)acrylate), tetrahydrofurfuryl (meth)acrylate, (meth)acrylamide, N,N'-dimethylmethacrylamide, N,N'-dimethylacrylamide ("DMA"), N-vinyl-2-pyrrolidone (or other N-vinyl lactams), N-vinyl acetamide, and combinations thereof. Still further examples of hydrophilic monomers are the vinyl carbonate and vinyl carbamate monomers disclosed in U.S. Pat. No. 5,070,215, and the hydrophilic oxazolone monomers disclosed in U.S. Pat. No. 4,910,277. The contents of these patents are incorporated herein by reference. The hydrophilic monomer also can be an anionic monomer, such as 2-methacryloyloxyethylsulfonate salts. Substituted anionic hydrophilic monomers, such as from acrylic and methacrylic acid, can also be utilized wherein the substituted group can be removed by a facile chemical process. Non-limiting examples of such substituted anionic hydrophilic monomers include trimethylsilyl esters of (meth)acrylic acid, which are hydrolyzed to regenerate an anionic carboxyl group. The hydrophilic monomer also can be a cationic monomer selected from the group consisting of 3-methacrylamidopropyl-N,N,N-trimethyammonium salts, 2-methacryloyloxyethyl-N,N,N-trimethylammonium salts, and amine-containing monomers, such as 3-methacrylamidopropyl-N,N-dimethyl amine. Other suitable hydrophilic monomers will be apparent to one skilled in the art.

Generally, a packaging system for the storage of an ophthalmic lens according to the present invention includes at least a sealed container containing one or more unused ophthalmic lenses immersed in an aqueous lens packaging solution. Preferably, the sealed container is a hermetically sealed blister-pack, in which a concave well containing a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

Organosilicon containing substrates are generally hydrophobic. To improve the patient experience, especially as regards to comfort, it is not unusual to utilize a packaging solution or other method to reduce the hydrophobic character of the substrate or to provide a ready to use product with improved lubricity. The relative hydrophobic character of a surface can be measured by many means known to those of ordinary skill in the art. One example of a method of contact angle measurement is Sessile Drop technique. For organosilicon containing substrates a high sessile drop contact angle is some indication of a relatively hydrophobic material (in the dry state). Based upon empirical observations, packaging solutions that provide a material having a sessile drop contact angle less than about 75 degrees are relatively hydrophilic and tend to easily slide about a hydrophobic surface such as that provided by a polystyrene Petri dish when a force such as applied by a hand held scalpel is used to slice the material (in this case a molded contact lens). Other packaging materials that provide a material having a sessile drop contact angle greater than about 75 degrees are relatively hydrophobic and tend to adhere to a hydrophobic surface such as that provided by a polystyrene Petri dish. It has surprisingly been discovered that when a organosilicon hydrogel material is packaged with a borate buffered polyphosphocholine solution the lens behaves as if it were packaged with a more hydrophobic material providing packaging solution (e.g., sessile drop contact angle greater than about 75 degrees) yet behaves as lubricious as a material packaged with a packaging solution that provides a material having a sessile drop contact angle less than about 75 degrees. Therefore a medical device packaged with a borate buffered polyphosphocholine solution is a preferred embodiment of the invention herein.

Suitable packaging solution material selection will depend upon a particular lens formulation and is therefore somewhat broad in nature. Below are nonlimiting examples of representative cationic, anionic, and zwitterionic polymers or components, along with non-ionic surfactants and peptide-based materials which are useful in packaging solutions (depending upon the intended use).

Anionic Polymers
   Poly(acrylic acid)
   Poly(acrylamide-co-acrylic acid)
   Carboxymethylcellulose
Cationic Polymers
   Polymer JR
   Polymers having latent amines
Zwitterionic Components
   Phosphocholine
   Latent amino acids
Polypeptides
   Poly(glutamic acid)
   Poly(lysine)
Non-Ionic Surfactants
   Tetronic T1107
   Tetronic T908
   Hydroxypropyl methylcellulose
   Silicone surfactants (NVP-co-TRIS VC)
   Glycereth cocoate For the sake of simplicity the following discussion of packaging solutions will focus upon nonionic polymeric conditioning agents. It will be recognized that in general the selection of an appropriate packaging solution for the ophthalmic device formed from a polymerized monomer mix containing monomers based on mono ethylenically unsaturated polymerizable group containing polycarbosiloxane monomers is within the purview of one of ordinary skill in the art. However, as noted above, certain packaging solutions used with an organosilicon containing device may be inventive in their own right.

Any suitable nonionic polymeric conditioning agent component may be employed in accordance with the present invention provided that it functions as described herein and has no substantial detrimental effect on the contact lens being stored or on the wearer of the contact lens. This component is ophthalmically acceptable at the concentrations used. Particularly useful components are those, which are water soluble, for example, soluble at the concentrations used in the presently useful liquid aqueous media.

These compounds condition the lens by providing one or more of the following attributes: increased viscosity for increased retention time on the lens; enhanced wetting of the lens surface; decreased surface friction (i.e., improved lubricity); or enhanced comfort of a contact lens by forming a cushioning film over the lens surface.

A class of nonionic, polymeric conditioning agents includes nonionic polysaccharides. Representative examples of suitable components for use herein include, but are not limited to, methylcellulose; hydroxyethylcellulose; hydroxypropylcellulose; hydroxypropylmethylcellulose; and methylhydroxyethyl starches.

Another class of nonionic, polymeric conditioning agents includes polyvinylalcohols and polyvinylpyrrolidones.

Another class of nonionic, polymeric conditioning agents includes polymers of PEO, including PEO homopolymers, and block copolymers of PEO and PPO. This class includes poloxamers and poloxamines, including those disclosed in U.S. Pat. No. 6,440,366.

The above classes of nonionic, polymeric conditioning agents are intended for illustrative purposes only and not to limit the scope of the present invention. Such polymers are known to those of skill in the art.

Generally, the average molecular weight of nonionic, polymeric conditioning agent is a minimum of about 1 kDa and a maximum of about 700 kDa, more preferably, about 5 kDa to 500 kDa.

The amount of nonionic, polymeric conditioning agent employed is that amount effective to improve the surface properties of the ophthalmic device when combined with a nonionic, nonpolymeric polyol. Preferably the nonionic, polymeric conditioning agent is present in the packaging solution of the invention in an amount of at least 0.01% w/v. The specific amount of such component used can vary widely depending on a number of factors, for example, the specific polymeric component and nonionic polyol being employed. Generally, the concentration of the nonionic, polymeric conditioning agent is from about 0.01 to about 10% w/w and preferably from about 0.5 to about 1.5% w/w.

In one embodiment, the nonionic, nonpolymeric polyol for use herein can be a nonionic polyol containing 2 to about 12 carbon atoms and preferably 2 to 4 carbon atoms and from 2 to 8 hydroxyl groups. Representative examples of such nonionic polyols include glycerin, ethylene glycol, propylene glycol, sorbitol, mannitol, monosaccharides, disaccharides such as trehalose, and the like and mixtures thereof. In one embodiment, the nonionic polyol can be glycerin, ethylene glycol, sorbitol, mannitol, monosaccharides and mixtures thereof.

The amount of the nonionic, nonpolymeric polyol in the packaging solution will generally be an amount sufficient to form a more uniform coating on the surface of the lens when packaged in a packaging solution according to the present invention. In general, the concentration of the nonionic polyol will ordinarily range from about 0.01 to about 10% w/w and preferably from about 0.1 to about 3.0% w/w.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations. The solution should be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions should be maintained within the range of about 6.0 to about 8, and preferably about 6.5 to about 7.8. Suitable buffers may be added, such as: phosphate; borate; citrate; carbonate; tris-(hydroxymethyl) aminomethane (TRIS); bis(2-hydroxyethyl)-imino-tris-(hydroxymethyl)aminoalcohol (bis-tris); zwitterionic buffers such as N-[2-Hydroxy-1,1-bis(hydroxymethyl)ethyl]glycine (Tricine) and N-[2-Hydroxy-1,1-bis(hydroxymethyl)ethyl] glycine, MOPS; N-(Carbamoylmethyl)taurine (ACES); amino acids and amino acid derivatives; and mixtures thereof. Generally, buffers will be used in amounts ranging from about 0.05 to about 2.5 percent by weight, and preferably from about 0.1 to about 1.5 percent by weight of the solution. The packaging solutions of this invention preferably contain a borate buffer, containing one or more of boric acid, sodium borate, potassium tetraborate, potassium metaborate or mixtures of the same.

If needed, the solutions of the present invention may be adjusted with tonicity agents, to approximate the osmotic pressure of normal lacrimal fluids, which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution, which will cause stinging, and eye irritation.

Examples of suitable tonicity adjusting agents include, but are not limited to, sodium and potassium chloride, dextrose, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, preferably from about 200 to about 450 mOsm/kg, more preferably from about 250 to about 400 mOsm/kg, and most preferably from about 280 to about 370 mOsm/kg.

If desired, one or more additional components can be included in the packaging solution. Such additional component or components are chosen to impart or provide at least one beneficial or desired property to the packaging solution. Such additional components may be selected from components that are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetra acetate, alkali metal hexametaphosphate, citric acid, sodium citrate and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing an ophthalmic lens according to the present invention includes at least packaging the ophthalmic lens immersed in the aqueous contact lens packaging solution described above. The method may include immersing the ophthalmic lens in an aqueous contact lens solution prior to delivery to the customer/wearer directly following manufacture of the contact lens. Alternately, the packaging and storing in the solution of the present invention may occur at an intermediate point before delivery to the ultimate customer (wearer) but following manufacture and transportation of the lens in a dry state, wherein the dry lens is hydrated by immersing the lens in the contact lens packaging solution. Consequently, a package for delivery to a customer may include a sealed container containing one or more unused contact lenses immersed in an aqueous contact lens packaging solution according to the present invention.

In one embodiment, the steps leading to the present ophthalmic device packaging system include (1) molding an ophthalmic device in a mold comprising at least a first and second mold portion, (2) removing the lens from the mold portions; (3) introducing the packing solution of this invention and the ophthalmic lens into the container, and (4) sealing the container. Preferably, the method also includes the step of sterilizing the contents of the container. Sterilization may take place prior to, or most conveniently after, sealing of the container and may be effected by any suitable method known in the art, e.g., by balanced autoclaving of the sealed container at temperatures of about 120° C. or higher. Preferred packages are plastic blister packages, including a recess for receiving a contact lens and the package solution, where the recess is sealed with lidstock prior to sterilization of the package contents. Especially preferred packages would include a disposable package and package assembly for contact lenses. A single package comprises a flange with a well formed therein for holding a contact lens in solution. A flexible cover sheet extends over the flange and is sealed about the perimeter of the well to seal the lens and solution in the well. The cover sheet may be easily peeled from the flange by a user to access the lens held therein. First and second support structures are formed opposite each other and extend generally perpendicularly from the flange. The support structures are configured to stably support the package on a flat surface such as a table.

Each support structure includes a major wall and a minor wall lying in generally spaced, parallel planes to each other although the major and minor walls may interconnect or touch along one or more points thereof. In a preferred embodiment, the minor wall is located inwardly of a respective major wall.

A package assembly is also disclosed including a second package configured substantially the same as a first package wherein the first and second packages may be releasably attached to each other with the first and second support structures of each in meshing engagement with each other.

In certain embodiments, following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated.

The following examples are provided to enable one skilled in the art to practice the invention and are merely illustrative of the invention. The examples should not be read as limiting the scope of the invention as defined in the claims.

EXAMPLES

All solvents and reagents were obtained from commercially available sources and used as received.
Analytical Measurements
ESI-TOF MS:

The electrospray (ESI) time of flight (TOF) MS analysis was performed on an Applied Biosystems Mariner instrument. The instrument operated in positive ion mode. The instrument was mass calibrated with a standard solution containing lysine, angiotensinogen, bradykinin (fragment 1-5) and des-Pro bradykinin. This mixture provides a seven-point calibration from 147 to 921 m/z. The applied voltage parameters were optimized from signal obtained from the same standard solution. For exact mass measurements poly(ethylene glycol) (PEG), having a nominal $M_n$ value of 400 Da, was added to the sample of interest and used as an internal mass standard. Two PEG oligomers that bracketed the sample mass of interest were used to calibrate the mass scale. Samples were prepared as 30 mM solutions in isopropanol (IPA) with the addition of 2% by volume saturated NaCl in IPA. Samples were directly infused into the ESI-TOF MS instrument at a rate of 35 µL/min. A sufficient resolving power (6000 RP m/Δm FWHM) was achieved in the analysis to obtain the monoisotopic mass for each sample. In each analysis the experimental monoisotopic mass was compared to the theoretical monoisotopic mass as determined from the respective elemental compositions. In each analysis the monoisotopic mass comparison was less than 10 ppm error. It should be noted that uncharged samples have a sodium (Na) atom included in their elemental composition. This Na atom occurs as a necessary charge agent added in the sample preparation procedure. Some samples do not require an added charge agent since they contain a charge from the quaternary nitrogen inherent to their respective structure.

GC:

Gas chromatography was performed using a Hewlett Packard HP 6890 Series GC System. Purities were determined by integration of the primary peak and comparison to the normalized chromatograph.

NMR:

$^1$H-NMR characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

Mechanical properties and Oxygen Permeability:

Modulus and elongation tests were conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) was determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the premoistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, *Optom Vis Sci* 7 (12s): 95 (1997), the disclosure of which is incorporated herein in its entirety:

| MATERIAL NAME | REPOSITORY VALUES | LOWER LIMIT | UPPER LIMIT |
| --- | --- | --- | --- |
| Fluoroperm 30 | 26.2 | 24 | 29 |
| Menicon EX | 62.4 | 56 | 66 |
| Quantum II | 92.9 | 85 | 101 |

ABBREVIATIONS

NVP 1-Vinyl-2-pyrrolidone
TRIS 3-Methacryloxypropyltris(trimethylsiloxy)silane
HEMA 2-Hydroxyethyl methacrylate
v-64 2,2'-Azobis(2-methylpropionitrile)
EGDMA ethylene glycol dimethacrylate
BHT butylated hydroxytoluene

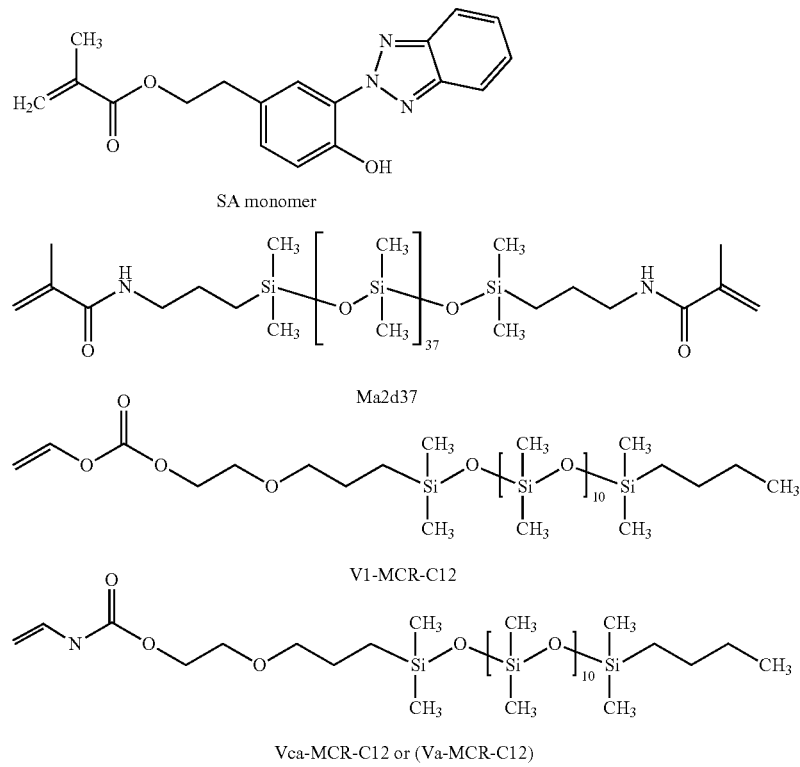

SA monomer

Ma2d37

V1-MCR-C12

Vca-MCR-C12 or (Va-MCR-C12)

Unless otherwise specifically stated or made clear by its usage, all numbers used in the examples should be considered to be modified by the term "about" and to be weight percent.

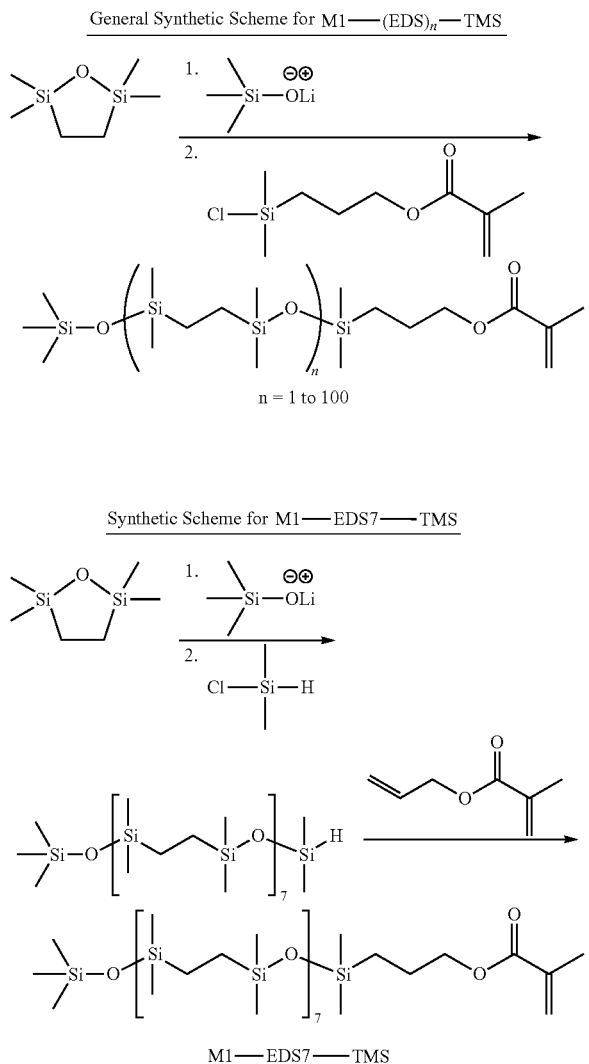

General Synthetic Scheme for M1—(EDS)$_n$—TMS n = 1 to 100

Synthetic Scheme for M1—EDS7—TMS

M1—EDS7—TMS

Example 1

Synthesis of M1-EDS7-TMS 2,2,5,5-tetramethyl-2,5-disila-1-oxacyclopentane (19.2 g, 0.12 mol) was taken in 50 mL of dry cyclohexane under N$_2$ and stirred for 30 minutes at 25° C. To this mixture lithium trimethylsilanolate (1.92 g, 0.02 mol) was added with stirring. After 1 hour dry THF (25 mL) was added and the reaction mixture continued to stir for 24 hours at 25° C. Dimethylchlorosilane (1.9 g, 0.02 mol) was then added and a color change was observed. Stirring was continued for 3 hours more and the reaction mixture was then filtered. The filtrate was concentrated under vacuum to give clear oil in 22 g yield as the expected product based on the method of preparation and characterized by NMR, SEC and MALDI showing about 7 condensed 2,2,5,5-tetramethyl-2,5-disila-1-oxacyclopentane ring open units. The filtrate was used as is for hydrosilation by taking into toluene (20 mL) and adding allylmethacrylate (3.15 g, 0.025 mol, 25 mmol) under N$_2$ atmosphere followed by the addition of platinum(0)1,3-divinyl-1,1,3,3-tetramethyl disiloxane complex 3 wt % solution in xylene (as catalyst). The reaction mixture was stirred for 6 hours at 40-45° C. Stripping of the solvent on rotovap and then under high vacuum to give a yellow oil in 17 g yield as the desired product M1-EDS7-TMS characterized by MALDI.

Example 2

Synthesis of M1-EDS6-TMS

To an oven dried 2 L two-neck round bottom flask equipped with a magnetic stirring bar and condenser under N2 atmosphere were added 2,2,5,5-tetramethyl-2,5-disila-1-oxacyclopentane (77.22 g, 0.482 mol) and anhydrous cyclohexane (150 mL) under stirring in N$_2$ atmosphere. Lithium trimethyl silanolate (7.2 g, 0.0749 mol) was added to the above reaction mixture followed by the addition of cyclohexane (25 mL). After stirring for one hour, THF (70 mL, distilled over Na/Benzophenone) was added and the reaction mixture continued to stir for 16 hours. Methylacryloxypropyl dimethylchlorosilane (20 g, 0.09 mol) was then added and the mixture stirred for another 24 hours. Reaction mixture was then filtered and Silica gel (3.5 g, dried at 160° C. for 3 hours) was then added and the reaction mixture stirred another 4 hours. Reaction mixture was then filtered thru a bed of Celite (20 g) and BHT (5 mg) was added to the filtrate. The filtrate was then concentrated under vacuum (40° C./0.3 mm Hg). Heptane (200 mL) was then added to the concentrate with shaking and washed with DI water (100 mL), aqueous NaHCO$_3$ (2×100 mL, prepared by dissolving 10 g NaHCO$_3$ in 200 mL DI water), brine (100 mL) and finally DI water (100 mL). Heptane (50 mL) was then added and dried over MgSO$_4$ (15 g) for 20 hours. MgSO$_4$ was filtered off and the solvent was removed on rotary evaporator. The crude product was stirred over activated basic Alumina (30 g for 24 h) and then filtered over a thin bed of Celite. Striping off any residue solvent at 25° C. at 0.2 mmHg for 30 minutes yielded the desired product M1-EDS6-TMS as a clear oil in 80 g quantity. It was characterized by NMR, GPC, GC-MS and MALDI.

Example 3

Synthesis of M1-EDS9-TMS 2,2,5,5-tetramethyl-2,5-disila-1-oxacyclopentane (14.4 g, 0.09 mol) was taken in 35 mL of dry cyclohexane under N$_2$ and stirred for 10 minutes at 25° C. To this lithium trimethylsilanolate (960 mg, 0.01 mol) was added with stirring. After 2 hours dry THF (20 mL) was added and the reaction mixture continued to stir for 24 hours at 25° C. Chlorodimethylsilylpropyloxy methacrylate (2.20 g, 0.01 mol) was then added and a color change was observed. Stirring was continued for 24 hours more and the reaction mixture was then quenched with 10 mg NaHCO$_3$. Cyclohexane (10 mL) was added with continued stirring for 2 hours more. The reaction mixture was then filtered over Celite. The filtrate was concentrated under vacuum to give clear oil in 16 g yield as the expected product M1-EDS9-TMS based on the method of preparation and characterized by NMR, SEC and MALDI.

Example 4

Synthesis of M1-EDS12-TMS 2,2,5,5-tetramethyl-2,5-disila-1-oxacyclopentane (19.2 g, 0.12 mol) was taken in 50 mL of dry cyclohexane under N$_2$ and stirred for 30 minutes at 25° C. To this mixture lithium trimethylsilanolate (960 mg, 0.01 mol) was added with stirring. After 2 hours dry THF (20 mL) was added and the reaction mixture continued to stir for 24 hours at 25° C. Chlorodimethylsilylpropyloxy methacrylate (2.20 g, 0.01 mol) was then added and a color change was observed. Stirring was continued for 24 hours more and the reaction mixture was then filtered over Celite. The filtrate was concentrated under vacuum to give clear oil in 20 g yield as the expected product M1-EDS12-TMS based on the method of preparation and characterized by NMR, SEC and MALDI.

Example 5

Synthesis of M1-EDS15-TMS 2,2,5,5-tetramethyl-2,5-disila-1-oxacyclopentane (24 g, 0.15 mol) was taken in 60 mL of dry cyclohexane under $N_2$ and stirred for 10 minutes at 25° C. To this lithium trimethylsilanolate (960 mg, 0.01 mol) was added with stirring. After 2 hours dry THF (20 mL) was added and the reaction mixture continued to stir for 24 hours at 25° C. Chlorodimethylsilylpropyloxy methacrylate (2.20 g, 0.01 mol) was then added and a color change was observed. Stirring was continued for 24 hours more and the reaction mixture was then quenched with 10 mg $NaHCO_3$. Cyclohexane (10 mL) was added with continued stirring for 2 hours more. The reaction mixture was then filtered over Celite. The filtrate was concentrated under vacuum to give clear oil in 25 g yield as the expected product M1-EDS15-TMS based on the method of preparation and characterized by NMR, SEC and MALDI.

Example 6

Synthesis of M1-BIS-EDS3-TMS

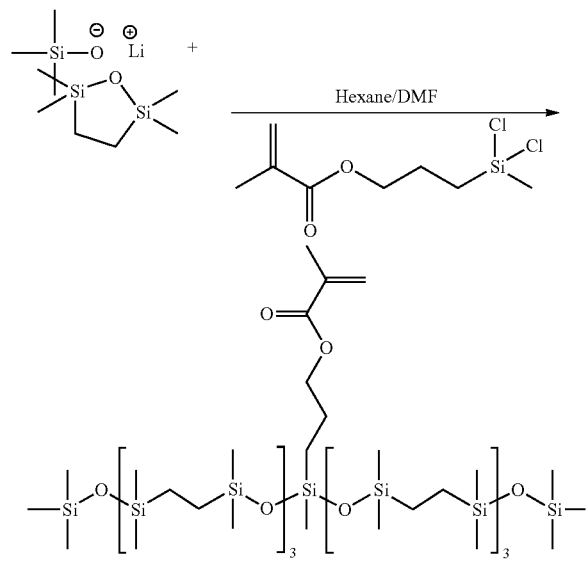

Lithium trimethyl silanolate (19.7 g, 0.2 mol) was suspended in anhydrous hexane (100 mL) in a 500 mL, round bottom flask was fitted with a mechanical stirrer, argon gas and a dropping funnel. A solution of 2,2,5,5-tetramethyl-2,5-disila-1-oxacyclopentane (32.07 g, 0.2 mol) in anhydrous hexane (100 mL), was quickly added to the flask with stirring. After an hour, the flask was cooled with an ice bath and DMF (50 mL) was added with continued stirring. After 4 hours, 3-methacryloxypropyl methyldichlorosilane (29 g, 0.12 mol) was added dropwise to the reaction mixture. The reaction mixture was stirred further for 24 hours at room temperature. Deionized water (50 mL) was then added to the flask with stirring. The organic layer was separated and dried over anhydrous sodium sulfate and filtered. The solvent was evaporated on a rotovap to give the desired product M1-BIS-EDS3-TMS in 40 g quantity as a clear, yellowish oil. The product was characterized by GC, GC/MS, IR and NMR.

Example 7

Synthesis of Dimethylammonium Methacrylamide (MA 1-Q-EDS9-TMS)

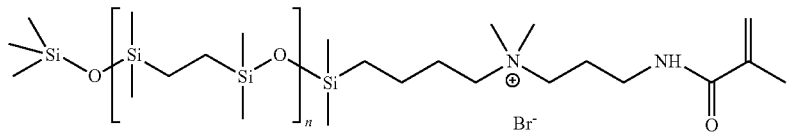

wherein n is 9.

2,2,5,5-tetramethyl-2,5-disila-1-oxacyclopentane (48 g, 0.3 mol) was taken in 55 mL of dry cyclohexane under $N_2$ and stirred for 30 minutes at 25° C. To this lithium trimethylsilanolate (4.8 g, 0.05 mol) was added with stirring. After 1 hour dry THF (25 mL) was added and the reaction mixture continued to stir for 24 hours at 25° C. Dimethylchlorosilane (5.1 g, 0.55 mol) was then added and a color change was observed. Stirring was continued for 3 hours more and the reaction mixture was then filtered. Filtrate was concentrated under vacuum to give clear oil in 42 g yield as the expected product based on the method of preparation and characterized by NMR, SEC and MALDI. 28.0 g of this was used for hydrosilation by taking into toluene (30 mL) and adding 1-bromobutene (4 g, 0.03 mol,) under $N_2$ atmosphere followed by the addition of platinum(0)1,3-divinyl-1,1,3,3-tetramethyl disiloxane complex 3 wt % solution in xylene (100 uL as catalyst). The reaction mixture was stirred for 4 hours at 45-50° C. and then at 25° C. for 48 hours. The reaction mixture was filtered over Celite using cotton plug. Stripping of the solvent on rotovap and then high vacuum to gave a yellow oil in 27 g yield as the desired bromo compound trimethylsilyloxy-[poly(dimethylsilyl-ethyl-dimethylsilyloxy)]-dimethylsilylbutylbomide characterized by MALDI with n=~9 units.

6.6 g (0.004 mol) of the bromo compound and 680 mg (0.004 mol) of dimethylaminopropyl methacrylamide were mixed together and stirred under $N_2$ for 6 hours at 25° C. Some exotherm was observed. Reaction mixture was subjected to high vacuum after 10 hours to give the desired product MA1-Q-EDS9-TMS in almost quantitative yield and characterized by NMR and MALDI.

Example 8

Synthesis of Comparative Monofunctional M1-MCR-C12

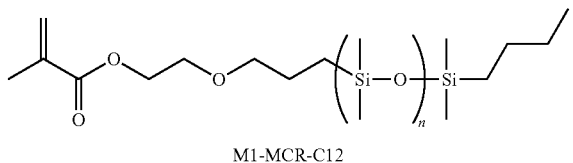

M1-MCR-C12 wherein n is 11.

Hydroxy ethoxypropyl terminated polydimethylsiloxane (50 grams, 0.048 mol) available from Gelest, Inc. (MCR-C12) was added to a 500 mL round bottom flask and dried via azeotropic distillation of toluene. To the flask was added anhydrous methylene chloride (200 mL) and triethylamine (17.12 g, 0.17 mol) and the reaction was stirred for minutes. The reaction flask was fitted with an addition funnel which was charged with methacryloyl chloride (17.18 g, 0.16 mol) and an additional 85 mL of anhydrous methylene chloride. The contents of the addition funnel were added to the reaction mixture dropwise at which time the addition funnel was exchanged with a reflux condenser. The reaction was then brought to reflux for 4 hours. After cooling the reaction mixture was filtered and placed in a separatory funnel where it was washed 2 times with 0.1 N HCl (150 mL); 2 times with sodium bicarbonate solution (150 mL) and 2 times with Brine solution (150 mL). The organic layer was then stirred with 10 grams of decolorizing carbon and 10 grams of silica gel for 24 hours and was then filtered and brought to dryness on a rotovap. The reaction yielded 45 g of a clear, yellow oil M1-MCR-C12 that was characterized by GC, NMR, and MALDI.

Example 9

Synthesis of Comparative Monofunctional MCA1-MCR-C12

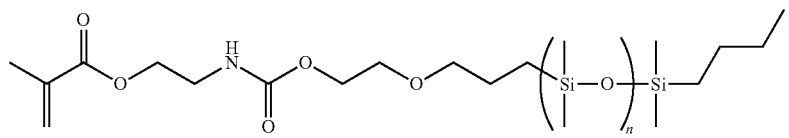

MCa1-MCR-C12 wherein n is 11.

Hydroxy ethoxypropyl terminated polydimethylsiloxane (200 grams, 0.193 mol) available from Gelest, Inc. (MCR-C12) was added to a 2 L round bottom flask and dried via azeotropic distillation of toluene. To the flask was added anhydrous methylene chloride (500 mL) and dibutyltin dilaurate (0.474 g, 0.0007 mol). The reaction flask was fitted with an addition funnel which was charged with 2-Isocyanatoethyl methacrylate (45.0 g, 0.290 mol) and an additional 100 mL of anhydrous methylene chloride. The contents of the addition funnel was then added to the reaction mixture dropwise and the reaction was stirred for 48 hours. 50 grams of silica gel (EMD Silica gel 60) was then added to the reaction mixture and stirred for 24 hours to scavenge excess isocyanatoethyl methacrylate. The reaction mixture was then filtered and concentrated on a rotovap yielding 210 g of a clear oil MCA1-MCR-C12 that was characterized by GC, NMR, and MALDI.

TABLE 1

Examples 10-23. Formulation of various EDS based monomers and comparative examples

| Example | Ma2D37 Methacrylamide Crosslinker | TRIS [tris(trimethyl-siloxy)silylpropyl methacrylate] | N-Vinyl Pyrolidone | N,N-Dimethyl-acrylamide | 2-Hydroxyethyl methacrylate | Hexanol | M1-MCR-C12 | MCa1-MCR-C12 |
|---|---|---|---|---|---|---|---|---|
| 10 | 9.5 | 35.5 | 30.8 | 4.7 | 4.7 | 4.7 | 9.5 | x |
| 11 | 9.5 | 35.5 | 30.8 | 4.7 | 4.7 | 4.7 | x | 9.5 |
| 12 | 9.5 | 35.5 | 30.8 | 4.7 | 4.7 | 4.7 | x | x |
| 13 | 9.5 | 35.5 | 30.8 | 4.7 | 4.7 | 4.7 | x | x |
| 14 | 9.5 | 35.5 | 30.8 | 4.7 | 4.7 | 4.7 | x | x |
| 15 | 9.5 | 35.5 | 30.8 | 4.7 | 4.7 | 4.7 | x | x |
| 16 | 9.5 | 35.5 | 30.8 | 4.7 | 4.7 | 4.7 | x | x |
| 17 | 9.5 | 29.9 | 25.9 | 4.0 | 4.0 | 19.9 | x | x |
| 18 | 0.0 | 32.5 | 28.1 | 4.3 | 4.3 | 13.0 | x | x |
| 19 | 9.5 | 35.5 | 30.8 | 4.7 | 4.7 | 4.7 | x | x |
| 20 | 9.5 | 35.5 | 30.8 | 4.7 | 4.7 | 4.7 | x | x |

TABLE 1-continued

Examples 10-23. Formulation of various EDS based monomers and comparative examples

| | | | | | | | | |
|---|---|---|---|---|---|---|---|---|
| 21 | 9.5 | 35.5 | 30.8 | 4.7 | 4.7 | 4.7 | x | x |
| 22 | 9.5 | 35.5 | 30.8 | 4.7 | 4.7 | 4.7 | x | x |
| 23 | 9.5 | 35.5 | 30.8 | 4.7 | 4.7 | 4.7 | x | x |

| Example | M1-EDS7-TMS | M1-EDS6-TMS | M1-EDS9-TMS | M1-EDS12-TMS | M1-EDS15-TMS | M2-EDS23 | M2-D27-EDS10 |
|---|---|---|---|---|---|---|---|
| 10 | x | x | x | x | x | x | x |
| 11 | x | x | x | x | x | x | x |
| 12 | 9.5 | x | x | x | x | x | x |
| 13 | x | 9.5 | x | x | x | x | x |
| 14 | x | x | 9.5 | x | x | x | x |
| 15 | x | x | x | 9.5 | x | x | x |
| 16 | x | x | x | x | 9.5 | x | x |
| 17 | x | x | 8.0 | x | x | 8.0 | x |
| 18 | x | x | 8.7 | x | x | x | 8.7 |
| 19 | x | x | x | x | x | x | x |
| 20 | x | x | x | x | x | x | x |
| 21 | x | x | x | x | x | x | x |
| 22 | x | x | x | x | x | x | x |
| 23 | x | x | x | x | x | x | x |

| Example | M1-Bis-D3-TMS | M1-Bis-EDS3-TMS | Ma1-Q-EDS9-TMS | V1-MCR-C12 | VCa1-MCR-C12 | Darocur 1173 | IMVT (concentration in ppm) |
|---|---|---|---|---|---|---|---|
| 10 | x | x | x | x | x | 0.47 | 90 |
| 11 | x | x | x | x | x | 0.47 | 90 |
| 12 | x | x | x | x | x | 0.47 | 90 |
| 13 | x | x | x | x | x | 0.47 | 90 |
| 14 | x | x | x | x | x | 0.47 | 90 |
| 15 | x | x | x | x | x | 0.47 | 90 |
| 16 | x | x | x | x | x | 0.47 | 90 |
| 17 | x | x | x | x | x | 0.47 | 90 |
| 18 | x | x | x | x | x | 0.47 | 90 |
| 19 | 9.5 | x | x | x | x | 0.47 | 90 |
| 20 | x | 9.5 | x | x | x | 0.47 | 90 |
| 21 | x | x | 9.5 | x | x | 0.47 | 90 |
| 22 | x | x | x | 9.5 | x | 0.47 | 90 |
| 23 | x | x | x | x | 9.5 | 0.47 | 90 |

Note:
The amounts presented in the table above are weight percentages in the formulation. Tint level is in ppm.

Preparation Procedure:

For examples 10-15, 17-23, 32, 54-56, 69 and 70, the specific monomer mixes set forth were prepared according to the table 1 above and tables 3, 5 and 6 below by weighing out various weight percentages of the components. Monomer mix was dispensed between polypropylene molds and prepared as lenses or flats in the case of Dk samples. Polymerization was carried out under UV light (~350 nm) for a period of two hours. After polymerization, the lenses or flats were released from the molds using 33% IPA in water and then extracted in 100% IPA for 4 hours. Lenses/Flats were then placed in deionized water for 30 minutes and packaged in vials containing 4 mL of borate buffered saline (BBS). Measured properties for the lenses/flats are shown in the table below.

TABLE 2

Selected Characteristics or processed lenses/flats containing EDS monomers and comparative examples.

| Example | Water Content (%) | Dk (barrers) | Modulus (gm/sqmm) | Elongation (%) | Tear Strength (gm/mm) | Advancing Contact Angle | Receding Contact Angle | Hysteressis |
|---|---|---|---|---|---|---|---|---|
| 10 | 42.3 | 96 | 92 (10) | 125 (52) | 7 (1) | 28 (4) | 19 (0) | 9 (4) |
| 11 | 43.0 | x | 107 (10) | 100 (30) | 4 (1) | 29 (2) | 21 (1) | 8 (1) |
| 12 | 47.3 | 93 | 58 (6) | 100 (30) | 4 (1) | 29 (2) | 21 (1) | 8 (1) |
| 13 | 40.8 | 87 | 91 (9) | 177 (25) | 5 (1) | 29 (3) | 21 (3) | 8 (6) |
| 14 | 42.1 | x | .3/17 | .3/17 | .3/17 | x | x | x |
| 15 | 35.7 | x | .3/17 | .3/17 | .3/17 | x | x | x |
| 17 | 42.0 | 95 | 74 (4) | 236 (25) | 7 (1) | x | x | x |
| 18 | 41.6 | 85 | 66 (5) | 143 (43) | 6 (1) | | | |
| 19 | 40.9 | x | 137 (6) | 157 (22) | x | x | x | x |
| 20 | 32.0 | x | 137 (8) | 137 (20) | x | x | x | x |
| 21 | 43.1 | x | 140 (6) | 96 (14) | x | x | x | x |
| 22 | 41.9 | x | 98 (10) | 159 (29) | 6 (0.4) | 98 (2) | 21 (1) | 76 (1) |
| 23 | 39.2 | x | 105 (5) | 125 (23) | 5 (1) | 96 (5) | 21 (1) | 76 (5) |

TABLE 2-continued

Selected Characteristics or processed lenses/flats containing EDS monomers and comparative examples.

| Example | Water Content (%) | Dk (barrers) | Modulus (gm/sqmm) | Elongation (%) | Tear Strength (gm/mm) | Advancing Contact Angle | Receding Contact Angle | Hysteressis |
|---|---|---|---|---|---|---|---|---|
| 32 | 46.9 | 91 | 71 (8) | 165 (74) | x | 31 (6) | 16 (1) | 15 (5) |
| 54 | 44.9 | x | 84 (10) | 177 (31) | 4 (1) | 33 (0.7) | 19 (1.0) | 14 (1.6) |
| 55 | 43.2 | x | 80 (7) | 176 (60) | 7 (1) | 40 (7.0) | 24 (2.3) | 16 (9.2) |
| 56 | 43.3 | x | 72 (4) | 159 (68) | 7 (0.3) | 41 (2.0) | 22 (1.4) | 19 (0.6) |
| 69 | 32.0 | x | 137 (8) | 137 (20) | x | x | x | x |
| 70 | 43 | 85 | 77 (6) | 200 (24) | 5 (0.2) | 39 (9.7) | 22 (1.5) | 17 (10.9) |

A 4502 Mechanical Tester MTS Instron was used to measure the modulus, tensile strength, percent elongation and tear strength of the lenses. Samples were tested in a water bath containing borate buffered saline.

Captive bubble contact angle data was collected on a First Ten Angstroms FTA-1000 Drop Shape Instrument. All samples were rinsed in HPLC grade water prior to analysis in order to remove components of the packaging solution from the sample surface. Prior to data collection the surface tension of the water used for all experiments was measured using the pendant drop method. In order for the water to qualify as appropriate for use, a surface tension value of 70-72 dynes/cm was expected. All lens samples were placed onto a curved sample holder and submerged into a quartz cell filled with HPLC grade water. Receding and advancing captive bubble contact angles were collected for each sample. The receding contact angle is defined as the angle measured in water as the air bubble is expanding across the sample surface (water is receding from the surface). The advancing contact angle is defined as the angle measured in water as the air bubble is retracting from the lens surface (water is advancing across the surface). All captive bubble data was collected using a high speed digital camera focused onto the sample/air bubble interface. The contact angle was calculated at the digital frame just prior to contact line movement across the sample/air bubble interface.

TABLE 3

Further examples of monomer mix formulations.

| Example | Ma2D37 Methacrylamide Crosslinker | TRIS [tris(trimethyl-siloxy)silylpropyl methacrylate] | N-Vinyl Pyrolidone | N,N-Dimethyl-acrylamide | 2-Hydroxyethyl methacrylate | Hexanol | M1-EDS6-TMS | Darocur 1173 | IMVT (concentration in ppm) |
|---|---|---|---|---|---|---|---|---|---|
| 24 | 0.1 | 41.2 | 58.1 | 0.0 | 0.0 | 0.0 | 0.1 | 0.48 | 90 |
| 25 | 4.7 | 38.4 | 29.2 | 1.9 | 7.6 | 4.4 | 13.3 | 0.47 | 90 |
| 26 | 7.0 | 30.5 | 20.5 | 3.0 | 7.0 | 4.7 | 27.0 | 0.48 | 90 |
| 27 | 11.1 | 29.4 | 27.7 | 2.6 | 6.0 | 4.0 | 18.8 | 0.43 | 90 |
| 28 | 32.3 | 28.0 | 13.8 | 4.3 | 4.3 | 4.0 | 12.9 | 0.43 | 90 |
| 29 | 44.7 | 12.9 | 23.0 | 0.0 | 4.2 | 3.9 | 10.9 | 0.42 | 90 |
| 30 | 59.7 | 9.6 | 14.3 | 0.0 | 4.8 | 4.5 | 6.7 | 0.48 | 90 |
| 31 | 75.8 | 0.0 | 0.0 | 9.5 | 9.5 | 4.7 | 0.1 | 0.47 | 90 |
| 32 | 6.6 | 35.5 | 30.8 | 4.7 | 4.7 | 4.7 | 12.3 | 0.47 | 90 |
| 33 | 4.5 | 9.0 | 58.8 | 4.5 | 0.0 | 13.6 | 9.1 | 0.45 | 90 |
| 34 | 6.1 | 18.2 | 18.2 | 1.2 | 1.2 | 48.6 | 6.1 | 0.30 | 90 |
| 35 | 7.7 | 23.1 | 23.1 | 1.5 | 1.5 | 34.6 | 7.7 | 0.48 | 90 |
| 36 | 15.9 | 15.9 | 23.9 | 4.0 | 4.0 | 19.9 | 15.9 | 0.40 | 90 |
| 37 | 5.0 | 10.0 | 29.9 | 5.0 | 5.0 | 14.9 | 29.9 | 0.50 | 90 |

Note:
The amounts presented in the table above are weight percentages in the formulation. Tint level is in ppm.

TABLE 4

Further examples of monomer mix formulations.

| Example | Ma2D37 Methacrylamide Crosslinker | TRIS [tris(trimethyl-siloxy)silylpropyl methacrylate] | N-Vinyl Pyrolidone | N,N-Dimethyl-acrylamide | 2-Hydroxyethyl methacrylate | Hexanol | M1-EDS6-TMS | Darocur 1173 | IMVT (concentration in ppm) |
|---|---|---|---|---|---|---|---|---|---|
| 38 | 0.1 | 41.2 | 58.1 | 0.0 | 0.0 | 0.0 | 0.1 | 0.48 | 145 |
| 39 | 4.7 | 38.4 | 29.2 | 1.9 | 7.6 | 4.4 | 13.3 | 0.47 | 145 |
| 40 | 7.0 | 30.5 | 20.5 | 3.0 | 7.0 | 4.7 | 27.0 | 0.48 | 145 |
| 41 | 11.1 | 29.4 | 27.7 | 2.6 | 6.0 | 4.0 | 18.8 | 0.43 | 145 |
| 42 | 32.3 | 28.0 | 13.8 | 4.3 | 4.3 | 4.0 | 12.9 | 0.43 | 145 |
| 43 | 44.7 | 12.9 | 23.0 | 0.0 | 4.2 | 3.9 | 10.9 | 0.42 | 145 |
| 44 | 59.7 | 9.6 | 14.3 | 0.0 | 4.8 | 4.5 | 6.7 | 0.48 | 145 |
| 45 | 75.8 | 0.0 | 0.0 | 9.5 | 9.5 | 4.7 | 0.1 | 0.47 | 145 |
| 46 | 6.6 | 35.5 | 30.8 | 4.7 | 4.7 | 4.7 | 12.3 | 0.47 | 145 |
| 47 | 4.5 | 9.0 | 58.8 | 4.5 | 0.0 | 13.6 | 9.1 | 0.45 | 145 |

TABLE 4-continued

Further examples of monomer mix formulations.

| Example | Ma2D37 Methacrylamide Crosslinker | TRIS [tris(trimethylsiloxy)silylpropyl methacrylate] | N-Vinyl Pyrolidone | N,N-Dimethylacryslamide | 2-Hydroxyethyl methacrylate | Hexanol | M1-EDS6-TMS | Darocur 1173 | IMVT (concentration in ppm) |
|---|---|---|---|---|---|---|---|---|---|
| 48 | 6.1 | 18.2 | 18.2 | 1.2 | 1.2 | 48.6 | 6.1 | 0.30 | 145 |
| 49 | 7.7 | 23.1 | 23.1 | 1.5 | 1.5 | 34.6 | 7.7 | 0.48 | 145 |
| 50 | 15.9 | 15.9 | 23.9 | 4.0 | 4.0 | 19.9 | 15.9 | 0.40 | 145 |
| 51 | 5.0 | 10.0 | 29.9 | 5.0 | 5.0 | 14.9 | 29.9 | 0.50 | 145 |

Note:
The amounts presented in the table above are weight percentages in the formulation. Tint level is in ppm.

TABLE 5

Further examples of monomer mix formulations.

| Example | Ma2D37 Methacrylamide Crosslinker | TRIS [tris(trimethylsiloxy)silylpropyl methacrylate] | N-Vinyl Pyrolidone | N,N-Dimethylacrylamide | 2-Hydroxyethyl methacrylate | Hexanol | Nonanol | t-Amyl alcohol | M1-EDS6-TMS | M1-BIS-EDS3-TMS | Darocur 1173 | IMVT (concentration in ppm) |
|---|---|---|---|---|---|---|---|---|---|---|---|---|
| 52 | 0.1 | 41.2 | 58.1 | 0.0 | 0.0 | 0.0 | 5.1 | 0.0 | 0.1 | 0.0 | 0.1 | 200 |
| 53 | 4.7 | 38.4 | 29.2 | 1.9 | 7.6 | 4.4 | 4.4 | 0.0 | 13.3 | 0.0 | 0.47 | 200 |
| 54 | 6.6 | 35.6 | 30.8 | 4.7 | 4.7 | 4.7 | 0.0 | 0.0 | 12.3 | 0.0 | 0.47 | 200 |
| 55 | 6.6 | 35.6 | 30.8 | 4.7 | 4.7 | 0.0 | 4.7 | 0.0 | 12.3 | 0.0 | 0.47 | 200 |
| 56 | 6.6 | 35.6 | 30.8 | 4.7 | 4.7 | 0.0 | 0.0 | 4.7 | 12.3 | 0.0 | 0.47 | 200 |
| 57 | 7.0 | 30.5 | 20.5 | 3.0 | 7.0 | 0.0 | 4.7 | 0.0 | 27.0 | 0.0 | 0.48 | 200 |
| 58 | 11.1 | 29.4 | 27.7 | 2.6 | 6.0 | 4.0 | 0.0 | 0.0 | 18.8 | 0.0 | 0.43 | 200 |
| 59 | 32.3 | 28.0 | 13.8 | 4.3 | 4.3 | 0.0 | 0.0 | 4.0 | 12.9 | 0.0 | 0.43 | 200 |
| 60 | 44.7 | 12.9 | 23.0 | 0.0 | 4.4 | 0.0 | 3.9 | 0.0 | 10.9 | 0.0 | 0.2 | 200 |
| 61 | 59.7 | 9.6 | 14.3 | 0.0 | 4.8 | 0.0 | 0.0 | 4.5 | 6.7 | 0.0 | 0.48 | 200 |
| 62 | 75.8 | 0.0 | 0.0 | 9.5 | 9.5 | 4.7 | 0.0 | 0.0 | 0.1 | 0.0 | 0.47 | 200 |
| 63 | 6.6 | 35.5 | 30.8 | 4.7 | 4.7 | 4.7 | 0.0 | 0.0 | 12.3 | 0.0 | 0.47 | 200 |
| 64 | 4.5 | 9.0 | 58.8 | 4.5 | 0.0 | 0.0 | 13.6 | 0.0 | 9.1 | 0.0 | 0.45 | 200 |
| 65 | 6.1 | 18.2 | 18.2 | 1.2 | 1.2 | 0.0 | 0.0 | 48.6 | 6.1 | 0.0 | 0.30 | 200 |
| 66 | 7.7 | 23.1 | 23.1 | 1.5 | 1.5 | 34.6 | 0.0 | 0.0 | 7.7 | 0.0 | 0.48 | 200 |
| 67 | 15.9 | 15.9 | 23.9 | 4.0 | 4.0 | 0.0 | 19.9 | 0.0 | 15.9 | 0.0 | 0.40 | 200 |
| 68 | 5.0 | 10.0 | 29.9 | 5.0 | 5.0 | 0.0 | 0.0 | 14.9 | 29.9 | 0.0 | 0.50 | 200 |
| 69 | 9.5 | 35.5 | 30.8 | 4.7 | 4.7 | 4.7 | 4.7 | 0.0 | 0.0 | 9.5 | 0.47 | 60 |

Note:
The amounts presented in the table above are weight percentages in the formulation. Tint level is in ppm.

TABLE 6

Further examples of monomer mix formulations.

| Example | Ma2D37 Methacrylamide Crosslinker | TRIS [tris(trimethylsiloxy)silylpropyl methacrylate] | N-Vinyl Pyrolidone | N,N-Dimethylacrylamide | 2-Hydroxyethyl methacrylate | Hexanol | Nonanol | t-Amyl alcohol | M1-EDS6-TMS | SA Monomer | Irgacure 819 | IMVT (concentration in ppm) |
|---|---|---|---|---|---|---|---|---|---|---|---|---|
| 70 | 7.0 | 34.6 | 30.6 | 4.7 | 4.7 | 0.0 | 4.7 | 0.0 | 12.6 | 0.6 | 0.5 | 200 |
| 71 | 9.5 | 35.5 | 35.3 | 7.7 | 4.7 | 4.7 | 0.0 | 0.0 | 0.0 | 2.0 | 0.47 | 200 |
| 72 | 0.1 | 41.2 | 58.1 | 0.0 | 0.0 | 0.0 | 5.1 | 0.0 | 0.1 | 0.5 | 0.1 | 200 |
| 73 | 4.7 | 38.4 | 29.2 | 1.9 | 7.6 | 4.4 | 4.4 | 0.0 | 13.3 | 1.1 | 0.47 | 200 |
| 74 | 6.6 | 35.6 | 30.8 | 4.7 | 4.7 | 4.7 | 0.0 | 0.0 | 12.3 | 0.0 | 0.47 | 200 |
| 75 | 6.6 | 35.6 | 30.8 | 4.7 | 4.7 | 0.0 | 4.7 | 0.0 | 12.3 | 0.0 | 0.47 | 200 |
| 76 | 6.6 | 35.6 | 30.8 | 4.7 | 4.7 | 0.0 | 0.0 | 4.7 | 12.3 | 0.0 | 0.47 | 200 |
| 77 | 7.0 | 30.5 | 20.5 | 3.0 | 7.0 | 0.0 | 4.7 | 0.0 | 27.0 | 0.0 | 0.48 | 200 |
| 78 | 11.1 | 29.4 | 27.7 | 2.6 | 6.0 | 4.0 | 0.0 | 0.0 | 18.8 | 0.0 | 0.43 | 200 |
| 79 | 32.3 | 28.0 | 13.8 | 4.3 | 4.3 | 0.0 | 0.0 | 4.0 | 12.9 | 0.0 | 0.43 | 200 |
| 80 | 44.7 | 12.9 | 23.0 | 0.0 | 4.4 | 0.0 | 3.9 | 0.0 | 10.9 | 0.0 | 0.2 | 200 |
| 81 | 59.7 | 9.6 | 14.3 | 0.0 | 4.8 | 0.0 | 0.0 | 4.5 | 6.7 | 0.0 | 0.48 | 200 |
| 82 | 75.8 | 0.0 | 0.0 | 9.5 | 9.5 | 4.7 | 0.0 | 0.0 | 0.1 | 0.0 | 0.47 | 200 |
| 83 | 6.6 | 35.5 | 30.8 | 4.7 | 4.7 | 4.7 | 0.0 | 0.0 | 12.3 | 0.0 | 0.47 | 200 |
| 84 | 4.5 | 9.0 | 58.8 | 4.5 | 0.0 | 0.0 | 13.6 | 0.0 | 9.1 | 0.0 | 0.45 | 200 |

TABLE 6-continued

Further examples of monomer mix formulations.

| Example | Ma2D37 Methacrylamide Crosslinker | TRIS [tris(trimethylsilyloxy)silylpropyl methacrylate] | N-Vinyl Pyrolidone | N,N-Dimethyl-acrylamide | 2-Hydroxyethyl methacrylate | Hexanol | Nonanol | t-Amyl alcohol | M1-EDS6-TMS | SA Monomer | Irgacure 819 | IMVT (concentration in ppm) |
|---|---|---|---|---|---|---|---|---|---|---|---|---|
| 85 | 6.1 | 18.2 | 18.2 | 1.2 | 1.2 | 0.0 | 0.0 | 48.6 | 6.1 | 0.0 | 0.30 | 200 |
| 86 | 7.7 | 23.1 | 23.1 | 1.5 | 1.5 | 34.6 | 0.0 | 0.0 | 7.7 | 0.0 | 0.48 | 200 |

Note:
The amounts presented in the table above are weight percentages in the formulation. Tint level is in ppm.

Step I

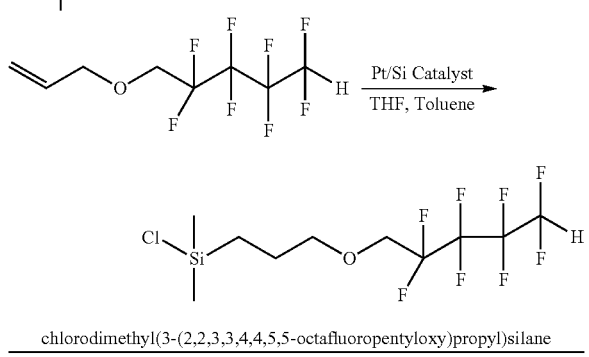

chlorodimethyl(3-(2,2,3,3,4,4,5,5-octafluoropentyloxy)propyl)silane

| Substance | Amount |
|---|---|
| Dimethylchlorosilane | 120 mL |
| Allyloxyoctafluoropentane | 200 g |
| Pt/Si catalyst | 640 µL |
| Anhydrous toluene | 250 mL |
| Anhydrous tetrahydrofuran | 250 mL |

Example 87

Capping of EDS with chlorodimethyl(3-(2,2,3,3,4,4,5,5-octafluoropentyloxy)propyl)silane In a 1000 mL three-neck round bottom flask fitted with a reflux condenser, thermo-controller, magnetic stirrer and Argon gas blanket, a mixture of dimethylchlorosilane, toluene and THF was added to the flask. Platinum(0)-1,3-divinyl-1,1,3,3-tetramethyl disiloxane was then added. The flask was heated to 60° C. for 7 hours. The reaction mixture exothermed at about 85° C. after about a half hour. A sample was withdrawn from the flask and checked by GC and showed a little starting material. The reaction was continued to run for about seven hours. The chlorodimethyl(3-(2,2,3,3,4,4,5,5-octafluoropentyloxy)propyl)silane was vacuum distilled at 70-80° C.

Step II 3-methacryloxypropyldimethylsilyloxy-EDS10-dimethylsilylpropyloxyoctafluoropentane Deionized water (100 mL) and diethyl ether (200 mL) were added to a single-neck 500 mL round-bottom flask fitted with a magnetic stirrer. The flask was cooled in an ice bath to 0° C. The flask was fitted with a dropping funnel and a mixture of (10 g, 0.045 mol) of 3-methacryloxypropyl dimethylchlorosilane and 50 mL of anhydrous THF was added to the flask. The reaction was stirred for one hour at 0° C. The organic layer was separated and dried over anhydrous sodium sulfate and filtered. The solvent was evaporated on a rotovap to give 3-methacryloxypropyl dimethylhydroxysilane in 9.0 g quantity, 99% yield as a clear, colorless oil.

The 3-methacryloxypropyl dimethylhydroxysilane (4 g, 0.02 mol) was added to a single-neck 500 mL round-bottom flask fitted with a magnetic stirrer. A 2.5 M n-BuLi (0.006 mol) mixture was slowly added to the flask. A mixture of 2,2,5,5-tetramethyl-2,5-disila-1-oxacyclopentane (65.3 g, 0.4 mol) and THF (50 mL) was added to the flask. The reaction stirred for 24 h. The chlorodimethyl(3-(2,2,3,3,4,4,5,5-octafluoropentyloxy)propyl)silane (7.1 g, 0.02 mol) was added to the flask and stirred for 24 h. The solvent was evaporated on a rotovap to give 3-methacryloxypropyldimethylsilyloxy-EDS10-dimethylsilylpropyloxyoctafluoropentane in 38 g quantity, 90% yield as a clear, colorless oil. The sample was checked by NMR spectroscopy, GCC-MS and MALDI.

Example 88

Ring opening of EDS with chlorodimethyl(3-(2,2,3,3,4,4,5,5-octafluoropentyloxy)propyl)silane Step I In a 250 mL one-neck round bottom flask fitted with a magnetic stirrer under nitrogen gas in an ice bath, water and ether were added and stirred. Chlorodimethyl(3-(2,2,3,3,4,4,5,5-octafluoropentyloxy)propyl)silane and THF was added to a dropping funnel and added dropwise to the water/ether mixture. The reaction was stirred at 0° C. for one hour. The product mixture was extracted with ether, dried with sodium sulfate, filtered and the ether was rotovapped off. The 3-dimethyl(3-(2,2,3,3,4,4,5,5-octafluoropentyloxy)propyl)silanol product was used in the next step of the reaction.

Step II

In a 500 mL, round bottom flask, fitted with a mechanical stirrer, Ar gas and a dropping funnel; 3-dimethyl(3-(2,2,3,3,4,4,5,5-octafluoropentyloxy)propyl)silanol product (7 g, 0.02 mol) was added. A 2.5 M n-BuLi (0.006 mol) mixture was slowly added to the flask followed by the addition of a solution of 2,2,5,5-tetramethyl-2,5-disila-1-oxacyclopentane (65 g, 0.4 mol) in THF (50 mL). The reaction was continued to stir for 24 hours. 3-(chlorodimethylsilyl)propyl methacrylate (4.84 g, 0.022 mol) was added to the reaction mixture and the stirring was further continued for 6 hours. After that solvent was evaporated under vacuum to afford the product that was characterized by NMR and MALDI.

Example 89

Improved Lubricity by Coating with Phosphoryl Choline

For each sample, a 0.5% solution in BBS was prepared by adding 1.25 g of polymer to BBS. The total volume of the solution was 250 mL. The pH of the solutions was 7.2. The test solution was poly(phosphocholine). Comparative solutions comprising separately Poly(acrylic acid)-450,000 g/mol, Tetronic TI 107, Tetronic T908, HPMC or Polymer JR were also prepared. All solutions were made at a concentration of 0.5% in BBS and pH was adjusted to 7.2 if needed (by standard techniques known in the art). For lens testing, 4.5 mL of each solution was added to a glass autoclave vial. An organosilicon-containing lens was placed in each vial and the system was capped with a Teflon-coated crimp cap. Each system was then autoclaved (121° C. for 30 minutes). The packaged lens was then removed from the package and rinsed with DI water. The rinsed lens was then placed on a polystyrene Petri dish and sectioned with a scalpel in order to cause the lens to lie flat.

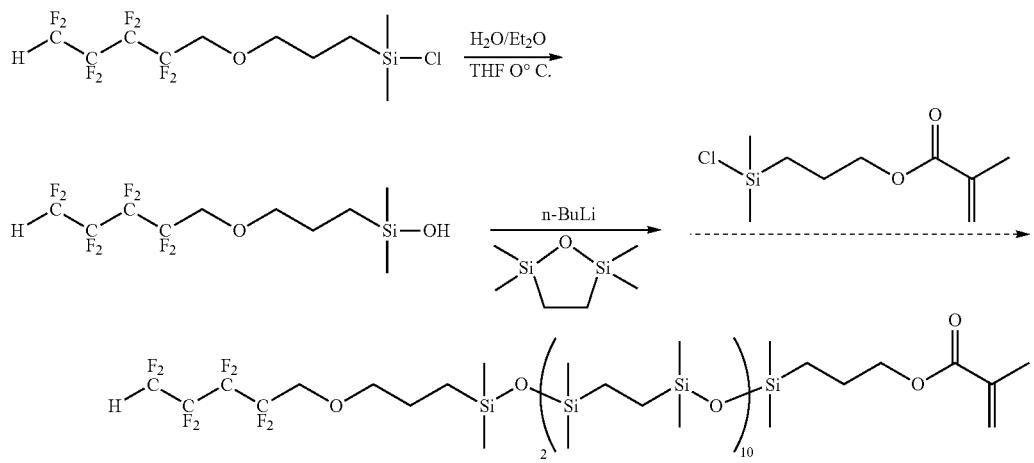

Preferred Embodiments

Disclosed in certain preferred embodiments of the invention herein is:

1. A monomer having a structural formula (I):

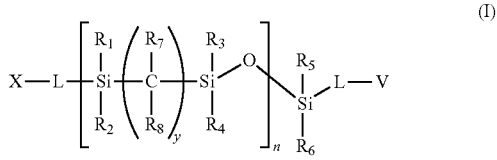

wherein X is the residue of a ring opening agent or a capping agent; L is the same or different and is a linker group or a bond; V is an ethylenically unsaturated polymerizable group;

$R_1$, $R_2$, $R_3$, $R_4$, $R_5$, $R_6$ are independently H, alkyl, halo alkyl, heteroalkyl, cyclo alkyl, heterocyclo alkyl, alkenyl, halo alkenyl, or aromatic; $R_7$ and $R_8$ when present are independently H or alkyl wherein at least one of $R_7$ or $R_8$ is hydrogen; y is 2-7 and n is 1-100.

2. A monomer having a structural formula (II)

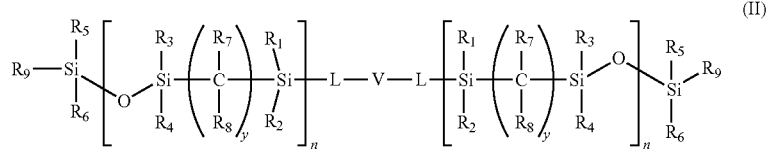

wherein L is the same or different and is a linker group or a bond and V is the same or different and is an ethylenically unsaturated polymerizable group, $R_1$, $R_2$, $R_3$, $R_4$, $R_5$, $R_6$ and $R_9$ are independently H, alkyl, halo alkyl, cyclo alkyl, heterocyclo alkyl, alkenyl, halo alkenyl, or aromatic, $R_7$ and $R_8$ are independently H or alkyl wherein at least one of $R_7$ or $R_8$ is hydrogen, y is 2-7 and n is 1-100.

3. A monomer according to preferred embodiment 1 wherein the X is a residue of a ring opening agent selected from the group consisting of alkyl lithiums, alkoxides, trialkylsiloxylithiums and acrylic ester-capped polysiloxane prepolymers in the presence of an acid catalyst.

4. The monomer of preferred embodiment 3 wherein the residue of the ring opening agent contains halo atoms.

5. The monomer of preferred embodiment 1 wherein linker group is selected from the group consisting of substituted or unsubstituted alkyl, alkyl ether, alkenyls, alkenyl ethers, halo alkyls, substituted or unsubstituted siloxanes, and monomers capable of propagating ring opening.

6. The monomer of preferred embodiment 2 wherein linker group is selected from the group consisting of substituted or unsubstituted alkyl, alkyl ether, alkenyls, alkenyl ethers, halo alkyls, substituted or unsubstituted siloxanes, and monomers capable of propagating ring opening.

7. The monomer of preferred embodiment 1 having a structural formula (III):

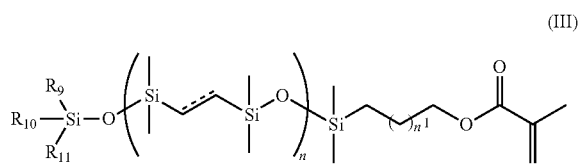

wherein $R_9$, $R_{10}$ and $R_{11}$ are independently H, alkyl, haloalkyl or other substituted alkyl groups, n is 1-100 and $n^1$ is 0-10.

8. The monomer of preferred embodiment 1 having a structural formula (IV):

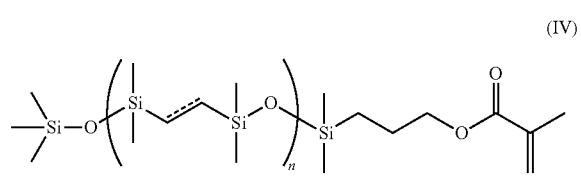

wherein n is 1-100.

9. The monomer of preferred embodiment 8 wherein n is 2-80.

10. The monomer of preferred embodiment 8 wherein n is 3-20.

11. The monomer of preferred embodiment 8 wherein n is 5-15.

12. A monomer of preferred embodiment 1 wherein V is selected from the group consisting of acrylates, methacrylates, vinyl carbonates, O-vinyl carbamates, N-vinyl carbamates, acrylamides and methacrylamides.

13. A monomer of preferred embodiment 2 wherein V is selected from the group consisting of acrylates, methacrylates, vinyl carbonates, O-vinyl carbamates, N-vinyl carbamates, acrylamides and methacrylamides.

14. The monomer of preferred embodiment 1 having a structural formula selected from the group consisting of the following structural formulae:

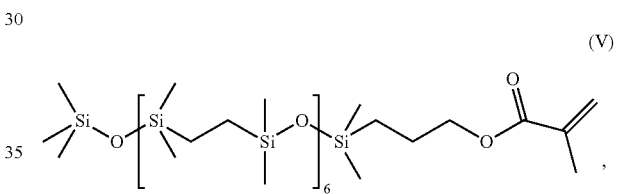

(V)

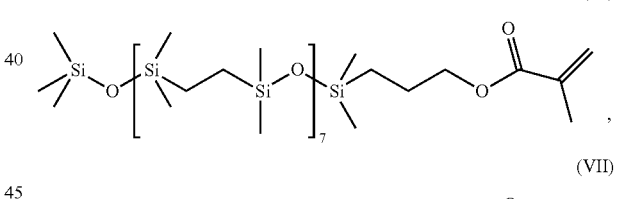

(VI)

(VII)

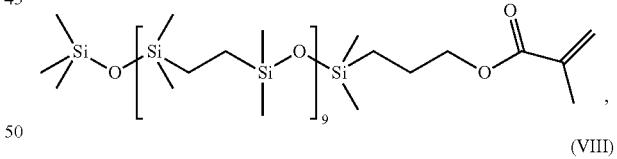

(VIII)

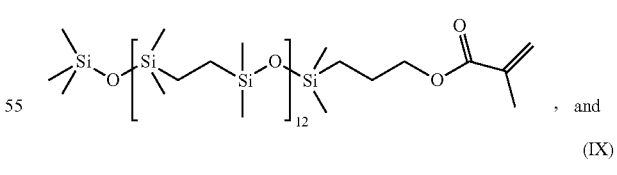

, and (IX)

.

15. The monomer of preferred embodiment 1 having a structural formula selected from the group consisting of the following structural formulae:

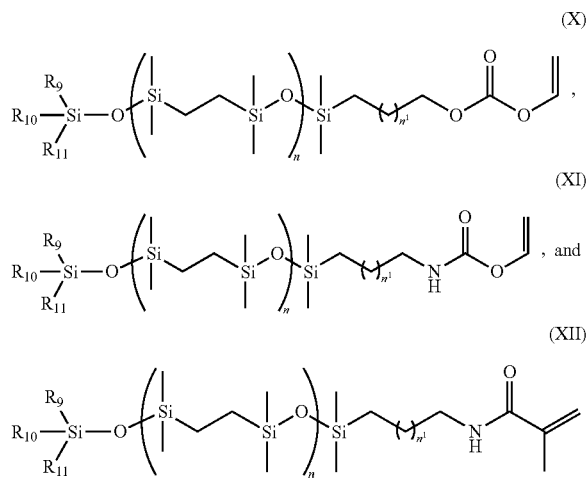

wherein $R_9$, $R_{10}$ and $R_{11}$ are independently H, alkyl, haloalkyl or other substituted alkyl groups and n is 1-100 and $n^1$ is 0-10.

16. The monomer of preferred embodiment 1 having a structural formula selected from the group consisting of the following structural formulae:

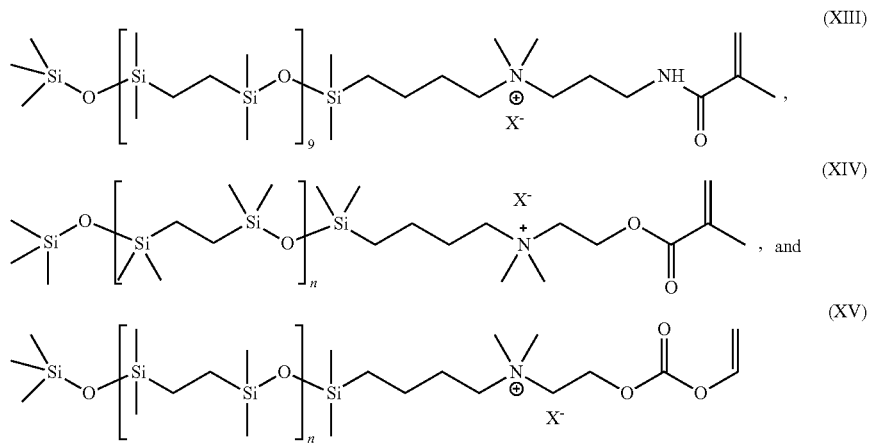

wherein n is 1-100 and $X^-$ a counterion to provide an overall neutral charge.

17. The monomer of preferred embodiment 1 having the following structural formula:

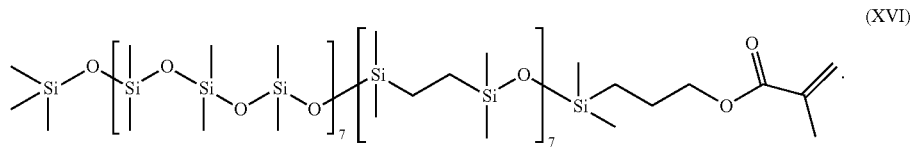

18. A monomer mix useful for forming a medical device wherein the monomer mix comprises at least one monomer selected from the group consisting of the monomers of preferred embodiment 1 and when polymerized forms a medical device.

19. A monomer mix useful for forming a medical device wherein the monomer mix comprises at least one monomer selected from the group consisting of the monomers of preferred embodiment 2 and when polymerized forms a medical device.

20. The monomer mix of preferred embodiment 18 further comprising a second copolymerizable second monomer.

21. The monomer mix of preferred embodiment 19 further comprising a second copolymerizable second monomer.

22. The monomer mix of preferred embodiment 18 wherein the medical device formed is selected from the group consisting of rigid contact lenses, soft contact lenses, phakic intraocular lenses, aphakic intraocular lenses and corneal implants.

23. The monomer mix of preferred embodiment 19 wherein the medical device formed is selected from the group consisting of rigid contact lenses, soft contact lenses, phakic intraocular lenses, aphakic intraocular lenses and corneal implants.

24. The monomer mix of preferred embodiment 18 wherein the medical device formed is selected from the group consisting of artificial heart valves, films, surgical devices, vessel substitutes, intrauterine devices, membranes, diaphragms, surgical implants, artificial blood vessels, artificial ureters, artificial breast tissue, membranes intended to come into contact with body fluid outside of the body, membranes for kidney dialysis machines, membranes for heart/lung machines, catheters, mouth guards, denture liners, ophthalmic devices, and hydrogel contact lenses.

25. The monomer mix of preferred embodiment 19 wherein the medical device formed is selected from the group consisting of artificial heart valves, films, surgical devices, vessel substitutes, intrauterine devices, membranes, diaphragms, surgical implants, artificial blood vessels, artificial ureters, artificial breast tissue, membranes intended to come into contact with body fluid outside of the body, membranes for kidney dialysis machines, membranes for heart/lung machines, catheters, mouth guards, denture liners, ophthalmic devices, and hydrogel contact lenses.

26. The monomer mix of preferred embodiment 24 wherein the medical device is a hydrogel contact lens.

27. The monomer mix of preferred embodiment 25 wherein the medical device is a hydrogel contact lens.

28. The monomer mix of preferred embodiment 18 wherein the at least one monomer selected from the group consisting of the monomers of preferred embodiment 1 is an mono ethylenically unsaturated polymerizable group containing polycarbosiloxane monomer.

29. The monomer mix of preferred embodiment 19 wherein the at least one monomer selected from the group consisting of the monomers of preferred embodiment 2 is an mono ethylenically unsaturated polymerizable group containing polycarbosiloxane monomer.

30. The monomer mix of preferred embodiment 28 wherein the mono ethylenically unsaturated polymerizable group containing polycarbosiloxane monomer is present in an amount from about 0.1 to about 30 percent by weight of the monomer mix.

31. The monomer mix of preferred embodiment 28 wherein the mono ethylenically unsaturated polymerizable group containing polycarbosiloxane monomer is present in an amount from about 0.1 to about 20 percent by weight of the monomer mix.

32. The monomer mix of preferred embodiment 28 wherein the mono ethylenically unsaturated polymerizable group containing polycarbosiloxane monomer is present in an amount from about 5 to about 15 percent by weight of the monomer mix.

33. The monomer mix of preferred embodiment 29 wherein the mono ethylenically unsaturated polymerizable group containing polycarbosiloxane monomer is present in an amount from about 0.1 to about 30 percent by weight of the monomer mix.

34. The monomer mix of preferred embodiment 29 wherein the mono ethylenically unsaturated polymerizable group containing polycarbosiloxane monomer is present in an amount from about 0.1 to about 20 percent by weight of the monomer mix.

35. The monomer mix of preferred embodiment 29 wherein the mono ethylenically unsaturated polymerizable group containing polycarbosiloxane monomer is present in an amount from about 5 to about 15 percent by weight of the monomer mix.

36. The monomer mix of preferred embodiment 20 wherein the second copolymerizable second monomer is a hydrophobic silicone containing monomer.

37. The monomer mix of preferred embodiment 36 wherein the hydrophobic silicone containing monomer is present in the monomer mix between about 0.1 to about 75.8 percent by weight.

38. The monomer mix of preferred embodiment 36 wherein the hydrophobic silicone containing monomer is present in the monomer mix between about 2 to about 20 percent by weight.

39. The monomer mix of preferred embodiment 36 wherein the hydrophobic silicone containing monomer is present in the monomer mix between about 5 to about 13 percent by weight.

40. The monomer mix of preferred embodiment 21 wherein the second copolymerizable second monomer is a hydrophobic silicone containing monomer.

41. The monomer mix of preferred embodiment 40 wherein the hydrophobic silicone containing monomer is present in the monomer mix between about 0.1 to about 75.8 percent by weight.

42. The monomer mix of preferred embodiment 40 wherein the hydrophobic silicone containing monomer is present in the monomer mix between about 2 to about 20 percent by weight.

43. The monomer mix of preferred embodiment 40 wherein the hydrophobic silicone containing monomer is present in the monomer mix between about 5 to about 13 percent by weight.

44. The monomer mix of preferred embodiment 20 wherein the second copolymerizable monomer is a non-silicone containing hydrophobic monomer.

45. The monomer mix of preferred embodiment 21 wherein the second copolymerizable monomer is a non-silicone containing hydrophobic monomer.

46. The monomer mix of preferred embodiment 20 wherein the non-silicone containing hydrophobic monomer is present at about 0 to about 60 percent by weight.

47. The monomer mix of preferred embodiment 21 wherein the non-silicone containing hydrophobic monomer is present at about 0 to about 60 percent by weight.

48. The monomer mix of preferred embodiment 20 wherein the non-silicone containing hydrophobic monomer is selected from the group consisting of alkyl acrylates and alkyl methacrylates.

49. The monomer mix of preferred embodiment 21 wherein the non-silicone containing hydrophobic monomer is selected from the group consisting of alkyl acrylates and alkyl methacrylates.

50. The monomer mix of preferred embodiment 20 wherein the second copolymerizable monomer is a bulky monomers selected from the group consisting of methacryloxypropyl tris(trimethylsiloxy)silane ("TRIS"), pentamethyldisiloxanyl methylmethacrylate, tris(trimethylsiloxy) methacryloxy propylsilane, phenyltretramethyldisloxanylethyl acrylate, methyldi(trimethylsiloxy) methacryloxymethyl silane, 3-[tris(trimethylsiloxy)silyl] propyl vinyl carbamate, 3-[tris(trimethylsiloxy)silyl]propyol allyl carbamate, and 3-[tris(trimethylsiloxy)silyl]propyl vinyl carbonate.

51. The monomer mix of preferred embodiment 21 wherein the second copolymerizable monomer is a bulky monomers selected from the group consisting of methacryloxypropyl tris(trimethylsiloxy)silane ("TRIS"), pentamethyldisiloxanyl methylmethacrylate, tris(trimethylsiloxy) methacryloxy propylsilane, phenyltretramethyldisloxanylethyl acrylate, methyldi(trimethylsiloxy) methacryloxymethyl silane, 3-[tris(trimethylsiloxy)silyl] propyl vinyl carbamate, 3-[tris(trimethylsiloxy)silyl]propyol allyl carbamate, and 3-[tris(trimethylsiloxy)silyl]propyl vinyl carbonate.

52. The monomer mix of preferred embodiment 50 wherein the bulky monomer is present at about 0 to about 41.2 percent by weight.

53. The monomer mix of preferred embodiment 50 wherein the bulky monomer is present at about 34 to about 41 percent by weight.

54. The monomer mix of preferred embodiment 50 wherein the bulky monomer is present at about 25 to about 41 percent by weight.

55. The monomer mix of preferred embodiment 51 wherein the bulky monomer is present at about 0 to about 41.2 percent by weight.

56. The monomer mix of preferred embodiment 51 wherein the bulky monomer is present at about 34 to about 41 percent by weight.

57. The monomer mix of preferred embodiment 51 wherein the bulky monomer is present at about 25 to about 41 percent by weight.

58. The monomer mix of preferred embodiment 26 wherein the monomer mix comprises a mixture containing at least one silicone-containing monomer and at least one hydrophilic monomer.

59. The monomer mix of preferred embodiment 26 wherein the monomer mix comprises a separate crosslinker.

60. The monomer mix of preferred embodiment 59 wherein the separate crosslinker is selected from the group consisting of methacrylates, ethylene glycol dimethacrylate (EGDMA) and allyl methacrylate (AMA).

61. The monomer mix of preferred embodiment 60 wherein the separate crosslinker is present at between about 0 to about 76 percent by weight.

62. The monomer mix of preferred embodiment 60 wherein the separate crosslinker is present at between about 2 to about 20 percent by weight.

63. The monomer mix of preferred embodiment 60 wherein the separate crosslinker is present at between about 5 to about 13 percent by weight.

64. The monomer mix of preferred embodiment 27 wherein the silicone-containing monomer is a crosslinking agent.

65. The monomer mix of preferred embodiment 20 wherein the second copolymerizable monomer is a hydrophilic monomer.

66. The monomer mix of preferred embodiment 65 wherein the hydrophilic monomer is selected from the group consisting of unsaturated carboxylic acids, methacrylic acids, acrylic acids; acrylic substituted alcohols, 2-hydroxyethyl methacrylate, 2-hydroxyethyl acrylate; vinyl lactams, N-vinylpyrrolidone (NVP), 1-vinylazonan-2-one; acrylamides, methacrylamide, N,N-dimethylacrylamide (DMA) and mixtures thereof.

67. The monomer mix of preferred embodiment 65 wherein the hydrophilic monomer is present, separately or by combined weight in amounts of between about 0 to about 60 percent by weight.

68. The monomer mix of preferred embodiment 65 wherein the hydrophilic monomer is present, separately or by combined weight in amounts between about 20 to about 45 percent by weight.

69. The monomer mix of preferred embodiment 65 wherein the hydrophilic monomer is present, separately or by combined weight in amounts between about 0 to about 48.6 percent by weight.

70. The monomer mix of preferred embodiment 65 wherein the hydrophilic monomer is present, separately or by combined weight in amounts between about 0 to about 30 percent by weight.

71. The monomer mix of preferred embodiment 65 wherein the hydrophilic monomer is present, separately or by combined weight in amounts between about 0 to about 25 percent by weight.

72. The monomer mix of preferred embodiment 65 wherein the hydrophilic monomer is present, separately or by combined weight in amounts between about 0 to about 9.5 percent by weight.

73. The monomer mix of preferred embodiment 65 wherein the hydrophilic monomer is present, separately or by combined weight in amounts between about 2 to about 7 percent by weight.

74. The monomer mix of preferred embodiment 21 wherein the second copolymerizable monomer is a hydrophilic monomer.

75. The monomer mix of preferred embodiment 74 wherein the hydrophilic monomer is selected from the group consisting of unsaturated carboxylic acids, methacrylic acids, acrylic acids; acrylic substituted alcohols, 2-hydroxyethyl methacrylate, 2-hydroxyethyl acrylate; vinyl lactams, N-vinylpyrrolidone (NVP), 1-vinylazonan-2-one; acrylamides, methacrylamide, N,N-dimethylacrylamide (DMA) and mixtures thereof.

76. The monomer mix of preferred embodiment 74 wherein the hydrophilic monomer is present, separately or by combined weight in amounts of between about 0 to about 60 percent by weight.

77. The monomer mix of preferred embodiment 74 wherein the hydrophilic monomer is present, separately or by combined weight in amounts between about 20 to about 45 percent by weight.

78. The monomer mix of preferred embodiment 74 wherein the hydrophilic monomer is present, separately or by combined weight in amounts between about 0 to about 48.6 percent by weight.

79. The monomer mix of preferred embodiment 74 wherein the hydrophilic monomer is present, separately or by combined weight in amounts between about 0 to about 30 percent by weight.

80. The monomer mix of preferred embodiment 74 wherein the hydrophilic monomer is present, separately or by combined weight in amounts between about 0 to about 25 percent by weight.

81. The monomer mix of preferred embodiment 74 wherein the hydrophilic monomer is present, separately or by combined weight in amounts between about 0 to about 9.5 percent by weight.

82. The monomer mix of preferred embodiment 74 wherein the hydrophilic monomer is present, separately or by combined weight in amounts between about 2 to about 7 percent by weight.

83. The monomer mix of preferred embodiment 36 further comprising an organic diluent.

84. The monomer mix of preferred embodiment 83 wherein the organic diluent is selected from the group consisting of alcohols, tert-butanol (TBA), tert-amyl alcohol, hexanol and nonanol; diols, ethylene glycol; polyols, glycerol and mixtures thereof.

85. The monomer mix of preferred embodiment 83 wherein the organic diluent is present at about 0 to about 60% by weight of the monomeric mixture.

86. The monomer mix of preferred embodiment 83 wherein the organic diluent is present at about 1 to about 40% by weight.

87. The monomer mix of preferred embodiment 83 wherein the organic diluent is present at about 2 to about 30% by weight.

88. The monomer mix of preferred embodiment 83 wherein the organic diluent is present at about 3 to about 25% by weight.

89. The monomer mix of preferred embodiment 40 further comprising an organic diluent.

90. The monomer mix of preferred embodiment 89 wherein the organic diluent is selected from the group consisting of alcohols, tert-butanol (TBA), tert-amyl alcohol, hexanol and nonanol; diols, ethylene glycol; polyols, glycerol and mixtures thereof.

91. The monomer mix of preferred embodiment 89 wherein the organic diluent is present at about 0 to about 60% by weight of the monomeric mixture.

92. The monomer mix of preferred embodiment 89 wherein the organic diluent is present at about 1 to about 40% by weight.

93. The monomer mix of preferred embodiment 89 wherein the organic diluent is present at about 2 to about 30% by weight.

94. The monomer mix of preferred embodiment 89 wherein the organic diluent is present at about 3 to about 25% by weight.

95. A hydrogel contact lens comprising a polymerized monomer mix comprising a polymerizable monomer mixture comprising about 0.1 to about 75.8 percent by weight of a methacrylamide crosslinker, about 0 to about 41.2 percent by weight of a bulky siloxane monomer, about 0 to about 78 percent by weight of at least one hydrophilic monomer, about 0 to about 48.6 percent by weight of an alcohol, about 0.1 to about 29.9 weight percent of an mono ethylenically unsaturated polymerizable group containing polycarbosiloxane monomer, about 0.1 to about 1.0 percent by weight of an initiator and about 90 to about 200 parts per million of a visibility tint.

96. The hydrogel contact lens of preferred embodiment 95 comprising as part of polymerizable monomer mixture comprising about 5 to about 13 percent by weight of a methacrylamide crosslinker, about 34 to about 41 percent by weight of a bulky siloxane monomer, about 28 to about 52 percent by weight of at least one hydrophilic monomer, about 0 to about 25 percent by weight of an alcohol, about 5 to about 15 weight percent of an mono ethylenically unsaturated polymerizable group containing polycarbosiloxane monomer, about 0.2 to about 0.8 percent by weight of an initiator and about 90 to about 145 parts per million of a visibility tint.

97. The hydrogel contact lens of preferred embodiment 95 comprising as part of polymerizable monomer mixture comprising about 2 to about 8 percent by weight of a methacrylamide crosslinker, about 25 to about 38 percent by weight of a bulky siloxane monomer, about 35 to about 45 percent by weight of at least one hydrophilic monomer, about 3 to about 8 percent by weight of an alcohol, about 10 to about 13 weight percent of an mono ethylenically unsaturated polymerizable group containing polycarbosiloxane monomer, about 0.3 to about 0.6 percent by weight of an initiator and about 145 to about 200 parts per million of a visibility tint.

98. A monomer mix useful for forming a medical device wherein the monomer mix comprises at least one monomer selected from the group consisting of any one of the monomers of preferred embodiments 1-17 and when polymerized forms an ophthalmic medical device to be implanted in or on an eye.

99. A medical device comprising a polymerized monomer mix of any one of embodiments 18-94.

100. The medical device of embodiment 99 wherein the medical device is coated with a polymer comprising at least one of the following monomers: HEMA, glyceryl methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), vinyl carbonate or vinyl carbamate monomers.

101. A method of making a medical device comprising providing a monomer mix which comprises at least one monomer selected from the group consisting of any one of the monomers of preferred embodiments 1-17 in a mold suitable for forming a medical device and exposing the mold containing the monomer mix to at least visible light at a sufficient intensity and for a sufficient period of time such that the monomer mix is polymerized and forms an ophthalmic medical device to be implanted in or on an eye.

102. A hydrogel contact lens system comprising a polymerized monomer mixture of any one of the monomer mixes of embodiments 18-94 placed in a package which comprises a flange with a well formed therein for holding a contact lens in solution, a flexible cover sheet which extends over the flange and is sealed about the perimeter of the well to seal the lens and solution in the well wherein the package has at least a first and second support structures formed opposite each other and extending generally perpendicularly from the flange wherein the support structures are configured to stably support the package on a flat surface.

103. The hydrogel contact lens system of embodiment 102 further comprising as a component of the packaging system a packaging solution comprising at least one component selected from the group consisting of anionic polymers such as Poly(acrylic acid), Poly(acrylamide-co-acrylic acid) or Carboxymethylcellulose; Cationic Polymers such as Polymer JR or polymers having latent amines; Zwitterionic components such as phosphocholine, polyphosphocholine or latent amino acids; Polypeptides such as Poly(glutamic acid) or Poly(lysine); Non-Ionic Surfactants such as Tetronic T1107, Tetronic T908, Hydroxypropyl methylcellulose, Silicone surfactants (NVP-co-TRIS VC) or Glycereth cocoate and mixtures any of the above packaging solution components.

104. The hydrogel contact lens system of embodiments 102 or 103 wherein each support structure includes a major wall and a minor wall lying in generally spaced, parallel planes to each other.

105. The hydrogel contact lens system of embodiment 104 wherein the major and minor walls interconnect or touch along one or more points thereof.

106. The hydrogel contact lens system of any one of embodiments 102-105 wherein the minor wall is located inwardly of a respective major wall.

107. A mono ethylenically unsaturated polymerizable group containing polycarbosiloxane monomer as substantially shown and described herein.

108. A monomer mix comprising a mono ethylenically unsaturated polymerizable group containing polycarbosiloxane monomer and at least one other monomer as substantially shown and described herein.

109. A medical device comprising a polymerized monomer mix comprising a mono ethylenically unsaturated polymerizable group containing polycarbosiloxane monomer and at least one other monomer as substantially shown and described herein.

110. The medical device of embodiment 109 wherein the medical device is coated with a coating material comprising at least one of the following materials HEMA, glyceryl methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), or derivatives thereof, hydrophilic vinyl carbonate or vinyl carbamate monomers as substantially shown and described herein.

111. A hydrogel contact lens system comprising a polymerized monomer mixture of any one of the monomer mixes of embodiments 18-94 placed in a package which comprises a flange with a well formed therein for holding a contact lens in solution, a flexible cover sheet which extends over the flange and is sealed about the perimeter of the well to seal the lens and solution in the well wherein the package has at least a first and second support structures formed opposite each other and extending generally perpendicularly from the flange wherein the support structures are configured to stably support the package on a flat surface wherein the solution is a packaging solution comprising at least one component selected from the group consisting of anionic polymers such as Poly(acrylic acid), Poly(acrylamide-co-acrylic acid) or Carboxymethylcellulose; Cationic Polymers such as Polymer JR or polymers having latent amines; Zwitterionic components such as phosphocholine, polyphosphocholine or latent amino acids; Polypeptides such as Poly(glutamic acid) or Poly(lysine); Non-Ionic Surfactants such as Tetronic T1107, Tetronic T908, Hydroxypropyl methylcellulose, Silicone surfactants (NVP-co-TRIS VC) or Glycereth cocoate and mixtures any of the above packaging solution components as substantially shown and described herein.

112. A method of making a hydrogel contact lens comprising as a comonomer in a polymerized monomer mixture a mono ethylenically unsaturated polymerizable group containing polycarbosiloxane monomer wherein the method is performed as substantially shown and described herein.

113. A hydrogel contact lens system comprising as part of a packaging solution in the hydrogel contact lens system polyphosphorylcholine.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A hydrogel contact lens comprising a polymerized monomer mix comprising a polymerizable monomer mixture comprising about 0.1 to about 75.8 percent by weight of a methacrylamide crosslinker monomer having multiple polymerizable methacrylamide functionalities, about 0 to about 41.2 percent by weight of a bulky siloxane monomer, about 0 to about 78 percent by weight of at least one hydrophilic monomer, about 0 to about 48.6 percent by weight of an alcohol, about 0.1 to about 29.9 weight percent of an mono ethylenically unsaturated polymerizable group containing polycarbosiloxane monomer, wherein a -[silyl-alkyl-siloxanyl]- group of the polycarbosiloxane monomer may be substituted at any atom capable of having a substituent group and about 0.1 to about 1.0 percent by weight of an initiator and about 90 to about 200 parts per million of a visibility tint.

2. The hydrogel contact lens of claim 1 comprising as part of polymerizable monomer mixture comprising about 5 to about 13 percent by weight of a methacrylamide crosslinker monomer having multiple polymerizable methacrylamide functionalities, about 34 to about 41 percent by weight of a bulky siloxane monomer, about 28 to about 52 percent by weight of at least one hydrophilic monomer, about 0 to about 25 percent by weight of an alcohol, about 5 to about 15 weight percent of an mono ethylenically unsaturated polymerizable group containing polycarbosiloxane monomer wherein the -[silyl-alkyl-siloxanyl]- group of the polycarbosiloxane monomer may be substituted at any atom capable of having a substituent group, about 0.2 to about 0.8 percent by weight of an initiator and about 90 to about 145 parts per million of a visibility tint.

3. The hydrogel contact lens of claim 1 comprising as part of polymerizable monomer mixture comprising about 2 to about 8 percent by weight of a methacrylamide crosslinker monomer having multiple polymerizable methacrylamide functionalities, about 25 to about 38 percent by weight of a bulky siloxane monomer, about 35 to about 45 percent by weight of at least one hydrophilic monomer, about 3 to about 8 percent by weight of an alcohol, about 10 to about 13 weight percent of an mono ethylenically unsaturated polymerizable group containing polycarbosiloxane monomer wherein the -[silyl-alkyl-siloxanyl]- group of the polycarbosiloxane monomer may be substituted at any atom capable of having a substituent group, about 0.3 to about 0.6 percent by weight of an initiator and about 145 to about 200 parts per million of a visibility tint.

4. The hydrogel contact lens of anyone of claims 1-3 wherein the mono ethylenically unsaturated polymerizable group containing polycarbosiloxane monomer is a monomer having a structural formula (I):

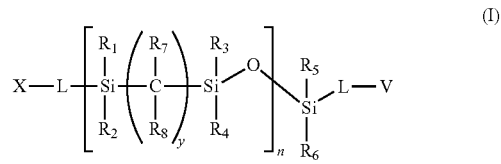

wherein X is the residue of a ring opening agent or a capping agent; L is the same or different and is a linker group or a bond; V is an ethylenically unsaturated polymerizable group; $R_1$, $R_2$, $R_3$, $R_4$, $R_5$, $R_6$ are independently H, alkyl, halo alkyl, heteroalkyl, cyclo alkyl, heterocyclo alkyl, alkenyl, halo alkenyl, or aromatic; $R_7$ and $R_8$ are, independently H or alkyl wherein at least one of $R_7$ or $R_8$ is hydrogen; y is 2-7 and n is 1-100.

5. The hydrogel contact lens of claim 1 wherein the mono ethylenically unsaturated polymerizable group containing polycarbosiloxane monomer is a monomer having a structural formula (II)

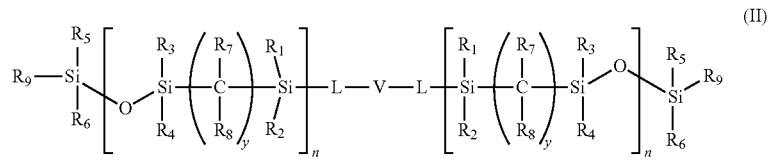

wherein L is the same or different and is a linker group or a bond and V is the same or different and is an ethylenically unsaturated polymerizable group, $R_1$, $R_2$, $R_3$, $R_4$, $R_5$, $R_6$ and $R_9$ are independently H, alkyl, halo alkyl, cyclo alkyl, heterocyclo alkyl, alkenyl, halo alkenyl, or aromatic, $R_7$ and $R_8$ are independently H or alkyl wherein at least one of $R_7$ or $R_8$ is hydrogen, y is 2-7 and n is 1-100.

6. The hydrogel contact lens of claim 4 wherein X is a residue of a ring opening agent selected from the group consisting of alkyllithiums, alkoxides, trialkylsiloxylithiums and acrylic ester-capped polysiloxane prepolymers in the presence of an acid catalyst.

7. The hydrogel contact lens of claim 4 wherein the linker group is selected from the group consisting of substituted or unsubstituted alkyl, alkyl ether, alkenyls, alkenyl ethers, halo alkyls, substituted or unsubstituted siloxanes, and monomers capable of propagating ring opening.

8. The hydrogel contact lens of claim 5 wherein the linker group is selected from the group consisting of substituted or unsubstituted alkyl, alkyl ether, alkenyls, alkenyl ethers, halo alkyls, substituted or unsubstituted siloxanes, and monomers capable of propagating ring opening.

9. The hydrogel contact lens of claim 4 wherein V is selected from the group consisting of acrylates, methacrylates, vinyl carbonates, O-vinyl carbamates, N-vinyl carbamates, acrylamides and methacrylamides.

10. The hydrogel contact lens of claim 5 wherein V is selected from the group consisting of acrylates, methacrylates, vinyl carbonates, O-vinyl carbamates, N-vinyl carbamates, acrylamides and methacrylamides.

11. The hydrogel contact lens of claim 1 wherein the polymerizable monomer mixture comprises about 28 to about 52 percent by weight of at least one hydrophilic monomer.

12. The hydrogel contact lens of claim 1 wherein the polymerizable monomer mixture comprises about 35 to about 45 percent by weight of at least one hydrophilic monomer.

13. The hydrogel contact lens of claim 1 wherein the lens is coated with a polymer containing a hydrophilic domain comprising at least one of 2-hydroxyethyl methacrylate, glycerol methacrylate, methacrylic acid, acrylic acid, methacrylamide, acrylamide, N,N'-dimethylmethacrylamide, N,N' dimethylacrylamide, ethylenically unsaturated poly(alkylene oxide)s, N-vinyl-2-pyrrolidone, vinyl carbonate, or vinyl carbamate monomers.

* * * * *